United States Patent
Wijdenes et al.

(10) Patent No.: US 9,758,581 B2
(45) Date of Patent: *Sep. 12, 2017

(54) HUMANIZED ANTI-CD4 ANTIBODY WITH IMMUNOSUPPRESSIVE PROPERTIES

(71) Applicant: BIOTEST AG, Dreieich (DE)

(72) Inventors: John Wijdenes, Larnod (FR); Helmut Jonuleit, Ginsheim-Gustavsburg (DE)

(73) Assignee: BIOTEST AG, Dreieich (DE)

( * ) Notice: Subject to any disclaimer, the term of this patent is extended or adjusted under 35 U.S.C. 154(b) by 658 days.

This patent is subject to a terminal disclaimer.

(21) Appl. No.: 14/176,485

(22) Filed: Feb. 10, 2014

(65) Prior Publication Data

US 2014/0220008 A1    Aug. 7, 2014

Related U.S. Application Data

(60) Continuation of application No. 12/392,556, filed on Feb. 25, 2009, now Pat. No. 8,685,651, which is a continuation of application No. 12/392,521, filed on Feb. 25, 2009, now Pat. No. 8,673,304, which is a division of application No. 12/246,660, filed on Oct. 7, 2008, now Pat. No. 8,586,715, said application No. 12/392,556 is a continuation of application No. 12/246,660, filed on Oct. 7, 2008, now Pat. No. 8,586,715, which is a continuation of application No. 11/217,402, filed on Sep. 2, 2005, now Pat. No. 7,452,981, which is a continuation of application No. PCT/EP2004/002888, filed on Mar. 19, 2004.

(30) Foreign Application Priority Data

Mar. 21, 2003 (EP) .................................... 03290725
Apr. 16, 2003 (EP) .................................... 03290942

(51) Int. Cl.
*A61K 39/395* (2006.01)
*C07K 16/28* (2006.01)
*A61K 39/00* (2006.01)

(52) U.S. Cl.
CPC .... *C07K 16/2812* (2013.01); *A61K 2039/505* (2013.01); *C07K 2317/24* (2013.01); *C07K 2317/56* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen et al. | |
| 5,604,209 A | 2/1997 | Ubasawa et al. | |
| 5,654,407 A | 8/1997 | Boyle et al. | |
| 5,690,933 A | 11/1997 | Cobbold et al. | |
| 5,777,085 A | 7/1998 | Co et al. | |
| 5,859,205 A | 1/1999 | Adair et al. | |
| 5,871,732 A | 2/1999 | Burkly et al. | |
| 5,886,152 A | 3/1999 | Nakatani et al. | |
| 6,037,454 A | 3/2000 | Jardieu et al. | |
| 6,056,956 A | 5/2000 | Cobbold et al. | |
| 6,270,766 B1 | 8/2001 | Feldman et al. | |
| 6,987,171 B1 | 1/2006 | Hunig | |
| 7,074,403 B1 | 7/2006 | Goldenberg et al. | |
| 7,125,679 B2 | 10/2006 | Ashkar | |
| 7,138,118 B2 | 11/2006 | Le et al. | |
| 7,304,127 B2 | 12/2007 | Saxinger et al. | |
| 7,338,658 B2 | 3/2008 | Hanna et al. | |
| 7,452,981 B2 | 11/2008 | Wijdenes et al. | |
| 7,722,873 B2 | 5/2010 | Lonberg et al. | |
| 7,838,489 B2 | 11/2010 | Feldmann et al. | |
| 7,846,442 B2 | 12/2010 | Feldmann et al. | |
| 8,440,806 B2 | 5/2013 | Wijdenes et al. | |
| 8,586,715 B2 | 11/2013 | Wijdenes et al. | |
| 8,673,304 B2 | 3/2014 | Wijdenes et al. | |
| 8,685,651 B2 | 4/2014 | Wijdenes et al. | |
| 9,334,325 B2 | 5/2016 | Osterroth et al. | |
| 2001/0056066 A1 | 12/2001 | Bugelski et al. | |
| 2002/0058029 A1 | 5/2002 | Hanna | |
| 2002/0068057 A1 | 6/2002 | Feldmann et al. | |
| 2002/0099179 A1 | 7/2002 | Jolliffe et al. | |
| 2002/0187526 A1 | 12/2002 | Ruben et al. | |
| 2003/0166860 A1 | 9/2003 | Hunig et al. | |
| 2003/0170239 A1 | 9/2003 | Hering et al. | |
| 2003/0219403 A1 | 11/2003 | Frewin et al. | |
| 2004/0092718 A1 | 5/2004 | Hunig | |
| 2004/0137000 A1 | 7/2004 | Lynn et al. | |
| 2004/0247594 A1 | 12/2004 | Hunig et al. | |
| 2006/0008457 A1 | 1/2006 | Hanke | |
| 2006/0009382 A1 | 1/2006 | Hanke et al. | |

(Continued)

FOREIGN PATENT DOCUMENTS

| | | |
|---|---|---|
| EP | 0344006 | 11/1989 |
| EP | 0449769 | 10/1991 |

(Continued)

OTHER PUBLICATIONS

Makrides (Protein Expression and Purification 17, 183-202 (1999).*
Wood et al. (Nat Rev Immunol. Mar. 2003;3(3):199-210).*
Kingley et al., J Immunol 2002;168;1080-1086.*
Van Maurik et al., The Journal of Immunology, 2002, 169: 5401-5404.*
Anderson, A. E., et al., "Tregs and Rheumatoid Arthritis," Acta Rheumatol. Port. 2008;33:17-33.
Biotest Analysis Conference, Mar. 20, 2008, pp. 0-38.
Biotest Half-Year Report of Jun. 30, 2008, pp. 1-16.
Cools, N., et al., "Regulatory T Cells and Human Disease," Clinical and Developmental Immunology, vol. 2007, pp. 1-11.
Dimasi, J. A., et al., "The price of innovation: new estimates of drug development costs," J. Health Economics 2003;22:151-185.

(Continued)

*Primary Examiner* — Zachary Skelding
(74) *Attorney, Agent, or Firm* — Shelly Guest Cermak; Cermak Nakajima & McGowan LLP

(57) ABSTRACT

A humanized antibody derived from mouse monoclonal anti-CD4 antibody B-F5 is able to activate CD25+CD4+ regulatory T cells and is useful for preparing immunosuppressive compositions.

15 Claims, 9 Drawing Sheets

(56) References Cited

U.S. PATENT DOCUMENTS

Figure 7:
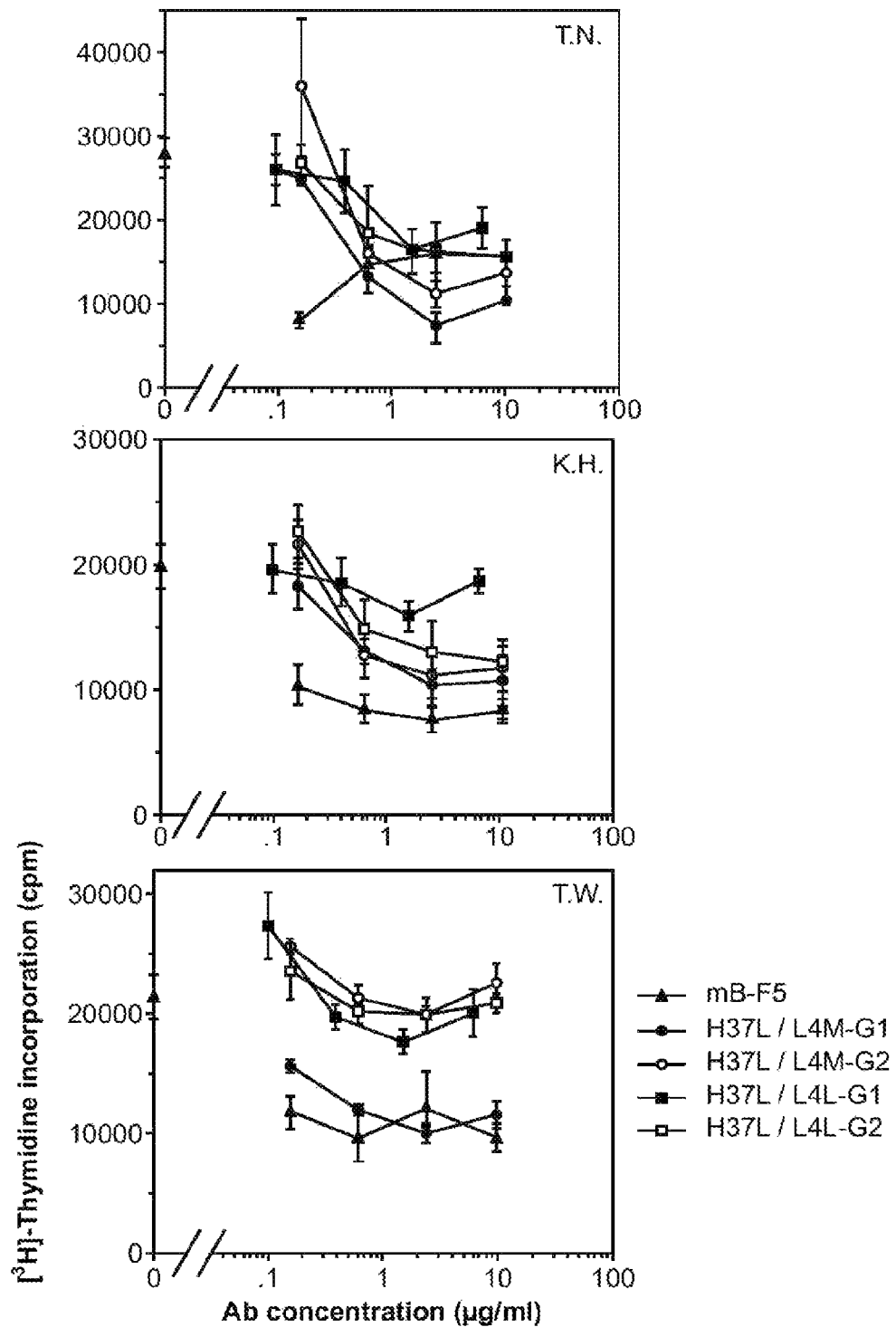
Figure 8:
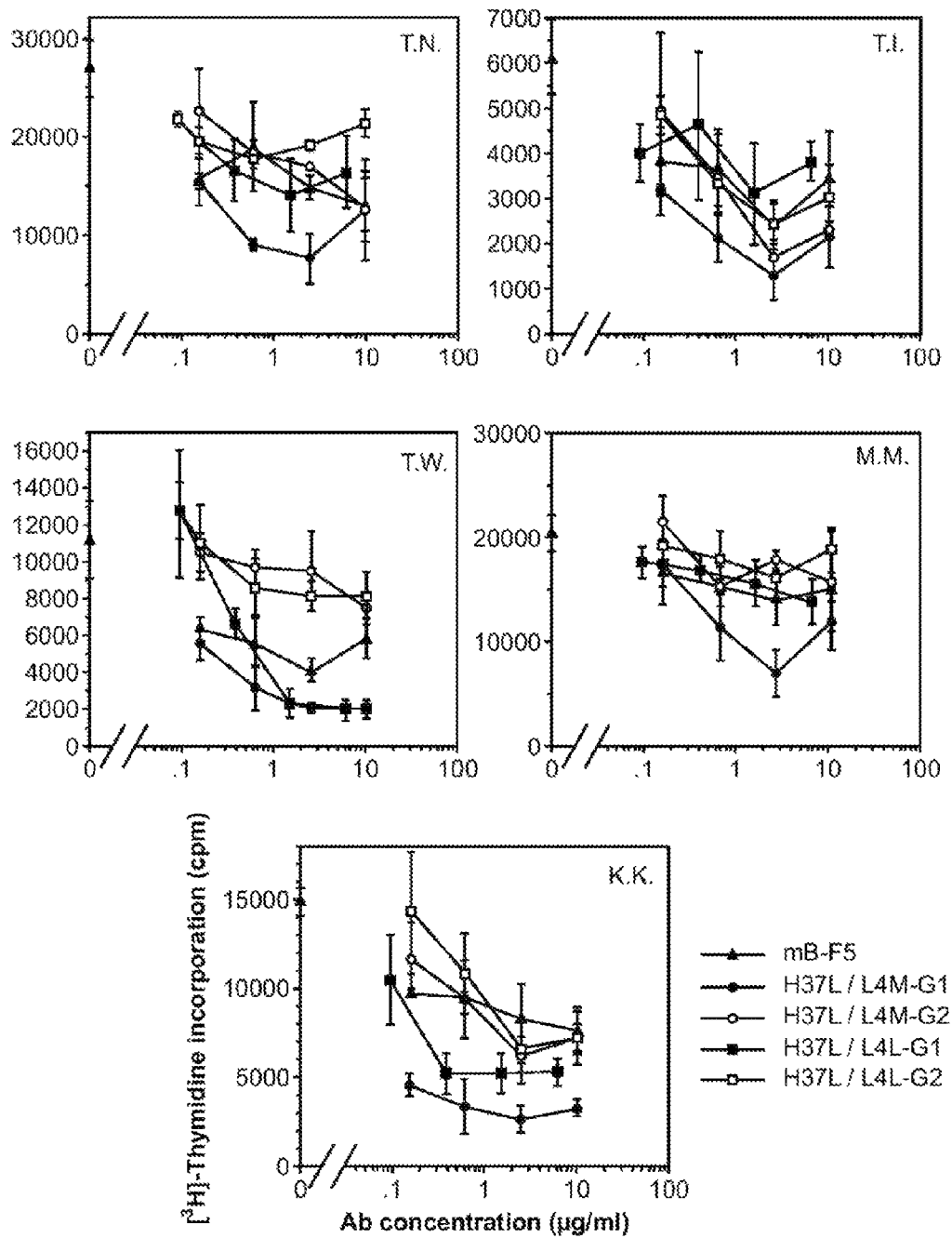

| | | | |
|---|---|---|---|
| 2006/0051346 | A1 | 3/2006 | Wijdenes |
| 2006/0121021 | A1 | 6/2006 | Hunig |
| 2006/0188493 | A1 | 8/2006 | Thomas |
| 2007/0077246 | A1 | 4/2007 | Koenig et al. |
| 2007/0166307 | A1 | 7/2007 | Bushell et al. |
| 2008/0213280 | A1 | 9/2008 | Benyunes |
| 2009/0104190 | A1 | 4/2009 | Wijdenes |
| 2009/0208496 | A1 | 8/2009 | Wijdenes |
| 2009/0208497 | A1 | 8/2009 | Wijdenes et al. |
| 2010/0291676 | A1 | 11/2010 | Wijdenes et al. |
| 2011/0059082 | A1 | 3/2011 | Germer et al. |
| 2011/0059083 | A1 | 3/2011 | Aigner et al. |
| 2011/0059084 | A1 | 3/2011 | Osterroth et al. |
| 2011/0229465 | A1 | 9/2011 | Osterroth et al. |
| 2013/0004513 | A1 | 1/2013 | Osterroth et al. |

FOREIGN PATENT DOCUMENTS

| | | |
|---|---|---|
| EP | 0568925 | 11/1993 |
| EP | 0929578 | 7/1999 |
| EP | 1161955 | 12/2001 |
| EP | 1241249 | 9/2002 |
| GB | 2376467 | 12/2002 |
| JP | 02-152989 | 6/1990 |
| JP | 2006-511516 | 4/2006 |
| WO | WO90/07861 | 7/1990 |
| WO | WO90/13562 | 11/1990 |
| WO | WO90/15152 | 12/1990 |
| WO | WO91/09966 | 7/1991 |
| WO | WO94/08619 | 4/1994 |
| WO | WO95/09652 | 4/1995 |
| WO | WO97/09351 | 3/1997 |
| WO | WO97/29131 | 8/1997 |
| WO | WO98/14211 | 4/1998 |
| WO | WO01/16182 | 3/2001 |
| WO | WO01/93908 | 12/2001 |
| WO | WO02/22212 | 3/2002 |
| WO | WO02/062335 A2 | 8/2002 |
| WO | WO02/085405 | 10/2002 |
| WO | WO02/102853 | 12/2002 |
| WO | WO2004/024097 | 3/2004 |
| WO | WO2004/050016 | 6/2004 |
| WO | WO2004/067554 | 8/2004 |
| WO | WO2004/112835 | 12/2004 |
| WO | WO2005/019254 | 3/2005 |

OTHER PUBLICATIONS

Feldmann, M., et al., "Role of cytokines in rheumatoid arthritis: an education in pathophysiology and therapeutics," Immunol. Rev. 2008;223:7-19.
Korn, T., et al., "Dynamics of antigen-specific regulatory T-cells in the context of autoimmunity," Seminars in Immunol. 2007;19:272-278.
Lobo, E. D., et al., "Antibody Pharmacokinetics and Pharmacodynamics," J. Pharm. Sci. 2004;93(11):2645-2668.
Mäkinen, H., et al., "Definition of remission for rheumatoid arthritis and review of selected clinical cohorts and randomised clinical trials for the rate of remission," Clin. Exp. Rheumatol. 2006;24(Suppl. 43):S22-S28.
MedLinePlus dictionary sponsored by the National Institutes of Health and the National Library of medicine, pp. 1-3, downloaded Nov. 14, 2014, see http://www.meriam-webster.com/medlineplus/dose.
Merriam Webster online dictionary definition of "dose," pp. 1-4, downloaded Nov. 14, 2014, http://www.meriam-webster.com/dictionary/dose.
Non-Final Office Action for co-pending U.S. Appl. No. 12/880,837 (Dec. 2, 2014).
Non-Final Office Action for co-pending U.S. Appl. No. 13/074,357 (Dec. 8, 2014).
Non-Final Office Action for co-pending U.S. Appl. No. 12/880,623 (Nov. 28, 2014).
Non-Final Office Action for co-pending U.S. Appl. No. 12/880,768 (Nov. 26, 2014).
Pincus, T., "Quantitative measure for assessing rheumatoid arthritis in clinical trials and clinical care," Best Practice & Research Clinical Rheumatology 2003;17(5):753-781.
Vajdos, F. F., et al., "Comprehensive Functional Maps of the Antigen-binding Site of an Anti-ErbB2 Antibody Obtained with Shotgun Scanning Mutagenesis," J. Mol. Biol. 2002;320:415-428.
Boshart, M., et al., "A Very Strong Enhancer Is Located Upstream of an Immediate Early Gene of Human Cytomegalovirus," Cell 1985;41:521-530.
Canva-Delcambre, V., et al., "Treatment of severe Crohn's disease with anti-CD4 monoclonal antibody," Aliment. Pharmacol. Ther. 1996;10:721-727.
Chothia, C., et al., "Conformation of immunoglobulin hypervariable regions," Nature 1989;342:877-883.
Chothia, C., et al., "Canonical Structures for the Hypervariable Regions of Immunoglobulins," J. Mol. Biol. 1987;196:901-917.
Cohen, J. L., et al., "CD4+CD25+ Immunoregulatory T Cells: New Therapeutics for Draft-Versus-Host Disease," J. Exp. Med. 2002;196(3):401-406.
Coloma, M. J., et al., "Primer Design for the Cloning of Immunoglobulin Heavy-Chain Leader-Variable Regions from Mouse Hybridoma Cells Using the PCR," BioTechniques 1991;11(2):152-156.
Dantal, J., et al., "Anti-CD4 MoAb Therapy in Kidney Transplantation—A Pilot Study in Early Prophylaxis of Rejection," Transplantation 1996;62(10):1502-1506.
Darby, C. R., et al., "Nondepleting Anti-CD4 Antibodies in Transplantation," Transplant. 1994;57(10):1419-1426.
Dieckmann, D., et al., "Ex Vivo Isolation and Characterization of CD4+CD25+ T Cells with Regulatory Properties from Human Blood," J. Exp. Med. 2001;193(11):1303-1310.
Edmundson, A. B., et al., "A Search for Site-Filling Ligands in the Mcg Bence-Jones Dimer: Crystal Binding Studies of Fluorescent Compounds," Mol. Immunol. 1984;21(7):561-576.
Felgner, P. L., et al., "Lipofection: A highly efficient, lipid-mediated DNA-transfection procedure," Proc. Natl. Acad. Sci. USA 1987;84:6413-7417.
Foote, J., et al., "Antibody Framework Residues Affecting the Conformation of the Hypervariable Loops," J. Mol. Biol. 1992;224:487-499.
Gillies, S. D., et al., "A Tissue-specific Transcription Enhancer Element Is Located in the Major Intron of a Rearranged Immunoglobulin Heavy Chain Gene," Cell 1983;33:717-728.
Goetzl, E. J., et al., "Affinity Labeling of a Mouse Myeloma Protein Which Binds Nitrophenyl Ligands. Kinetics of Labeling and Isolation of a Labeled Peptide," Biochemistry 1970;9(5):1267-1278.
Goldberg, D., et al., "Immunological Effects of High Dose Administration of Anti-CD4 Antibody in Rheumatoid Arthritis Patients," J. Autoimmun. 1991;4:617-630.
Gorman, C. M., et al., "The Rous sarcoma virus long terminal repeat is a strong promoter when introduced into a variety of eukaryotic cells by DNA-mediated transfection," Proc. Natl. Acad. Sci. USA 1982;79:6777-6781.
Gorman, S. D., et al., "Reshaping a therapeutic CD4 antibody," Proc. Natl. Acad. Sci. USA 1991;88:4181-4185.
Gottlieb, A. B., et al., "Anti-CD4 monoclonal antibody treatment of moderate to severe psoriasis vulgaris: Results of a pilot, multicenter, multiple-dose placebo-controlled study," J. Am. Acad. Dermatol. 2000;43:595-604.
Graham, F. L., et al., "A New Technique for the Assay of Infectivity of Human Adenovirus 5 DNA," Virology 1973;52:456-467.
Hoffmann, P., et al., "Donor-type CD4+CD25+ Regulatory T Cells Suppress Lethal Acute Graft-Versus-Host Disease after Allogenic Bone Marrow Transplantation," J. Exp. Med. 2002;196(3):389-399.
Jonuleit, H., et al., "Identification and Functional Characterization of Human CD4+CD25+ T Cells with Regulatory Properties Isolated from Peripheral Blood," J. Exp. Med. 2001;193(11):1285-1294.
Kabat, E. A., "Structure and Heterogeneity of Antibodies," Proc. 10th Congr. Eur. Soc. Haematl., Strasbourg Acta haemat. 1966;36:198-238.

(56) References Cited

OTHER PUBLICATIONS

Kettleborough, C. A., et al., "Humanization of a mouse monoclonal antibody by CDR-grafting: the importance of framework residues on loop conformation," Protein Eng. 1991;4(7):773-783.
Levings, M. K., et al., "Human CD4+CD25+ T Regulatory Cells Suppress Naïve and Memory T Cell Proliferation and Can Be Expanded In Vitro without Loss of Function," J. Exp. Med. 2001;193(11):1295-1301.
Lusky, M., et al., "Inhibition of SV40 replication in simian cells by specific pBR322 DNA sequences," Nature 1981;293:79-81.
Morel, P., et al., "Anti-CD4 Monoclonal Antibody Administration in Renal Transplanted Patients," Clin. Immunol. Immunopath. 1990;56:311-322.
Morel, P., et al., "Anti-CD4 Monoclonal Antibody Therapy in Severe Psoriasis," J. Autoimmun. 1992;5:465-477.
Mount, D. W., et al., "Microcomputer programs for back translation of protein to DNA sequences and analysis of ambiguous DNA sequences," Nucl. Acids Res. 1984;12(1):819-823.
Orlandi, R., et al., "Cloning immunoglobulin variable domains for expression by the polymerase chain reaction," Proc. Natl. Acad. Sci. USA 1989;86:3833-3837.
Osterburg, G., et al., "Computer programs for the analysis and the management of DNA sequences," Nucl. Acids Res. 1982;10(1):207-216.
Potter, H., et al., "Enhancer-dependent expression of human immunoglobulin genes introduced into mouse pre-B lymphocytes by electroporation," Proc. Natl. Acad. Sci. USA 1984;81:7161-7165.
Puls, R. L, et al., "Gene transfer and expression of a non-viral polycation-based vector in CD4+ cells," Gene Ther. 1999;6:1774-1778.
Racadot, E., et al., "Treatment of Multiple Sclerosis with Anti-CD4 Monoclonal Antibody," J. Autoimmun. 1993;6:771-786.
Reczko, M., et al., "Prediction of hypervariable CDR-H3 loop structures in antibodies," Protein Eng. 1995;8 (4):389-395.
Rep, M. H. G., et al., "Treatment with Depleting CD4 Monoclonal Antibody Results in a Preferential Loss of Circulating Naïve T Cells but Does Not Affect IFN-Secreting TH1 Cells in Humans," J. Clin. Invest. 1997;99(9):2225-2231.
Rumbach, L., et al., "Biological assessment and MRI monitoring of the therapeutic efficacy of a monoclonal anti-T CD4 antibody in multiple sclerosis patients," Multiple Sclerosis 1996;1:207-212.
Saitovitch, D., et al., "Kinetics of Induction of Transplantation Tolerance With a Nondepleting Anti-Cd4 Monoclonal Antibody and Donor-Specific Transfusion Before Transplantation: A Critical Period of Time Is Required for Development of Immunological Unresponsiveness," Transplant. 1996;61(11):1642-1647.
Sakaguchi, S., et al., "Immunologic Self-Tolerance Maintained by Activated T Cells Expressing IL-2 Receptor•-Chains (CD25)," J. Immunol. 1995;155:1151-1164.
Sastry, L., et al., "Cloning of the immunological repertoire in *Escherichia coli* for generation of monoclonal catalytic antibodies: Construction of a heavy chain variable region-specific cDNA library," Proc. Natl. Acad. Sci. USA 1989;86:5728-5732.
Schimke, R. T., "Gene Amplification in Cultured Animal Cells," Cell 1984;37:705-713.
Shevach, E. M., "Certified Professionals: CD4+CD25+ Suppressor T Cells," J. Exp. Med. 2001;193(11):F41-F45.
Skov, L., et al., "HuMax-CD4 a Fully Human Monoclonal Anti-CD4 Antibody for the Treatment of Psoriasis Vulgaris," Arch. Dermatol. 2003;139:1433-1439.
Southern, P. J., et al., "Transformation of Mammalian Cells to Antibiotic Resistance with a Bacterial Gene Under Control of the SV40 Early Region Promoter," J. Mol. Appl. Genetics 1982;1:327-341.
Subramani, S., et al., "Expression of the Mouse Dihydrofolate Reductase Complementary Deoxyribonucleic Acid in Simian Virus 40 Vectors," Mol. Cell. Biol. 1981;1(9):854-864.
Tak, P. P., et al., "Reduction of Synovial Inflammation After Anti-CD4 Monoclonal Antibody Treatment in Early Rheumatoid Arthritis," Arth, Rheum. 1995;38(1):1457-1465.

Takahashi, T., et al., "Immunologic self-tolerance maintained by CD4+CD25+ naturally anergic and suppressive T cells: induction of autoimmune disease by breaking their anergic/suppressive state," Internatl. Immunol. 1998;10 (12):1969-1980.
Taylor, P. A., et al., "The infusion of ex vivo activated and expanded CD4+CD25+ immune regulatory cells inhibits graft-versus-host disease lethality," Blood 2002;99(10):3493-3499.
Thornton, A. M., et al., "Suppressor Effector Function of CD4+CD25+ Immunoregulatory T Cells Is Antigen Nonspecific," J. Immunol. 2000;164:183-190.
Vieira, J., et al., "Production of Single-Stranded Plasmid DNA," Methods Enzymol. 1987;153:3-11.
Ward, S., et al., "Binding activities of a repertoire of single immunoglobulin variable domains secreted from *Escherichia coli*," Nature 1989;341:544-546.
American College of Rheumatology Subcommittee on Rheumatoid Arthritis. Guidelines for the management of rheumatoid arthritis: 2002 update. Arthritis Rheum. (2002) 46(2):328-46.
Biotest AG / Research Update; DGAP News: Biotest AG: Biotest monoclonal antibody BT-061 shows clear indications of efficacy in the treatment of psoriasis. Sep. 8, 2008, pp. 1-2.
Biotest AG Press release—Biotest Phase IIb study of Tregalizumab (BT-061) in moderate to severe rheumatoide Arthritis did not meet the primary endpoint—potential one time effect of up to—Eur 30 million, Apr. 24, 2015, pp. 1-3.
Biotest Autumn Conference for Journalists and Analysts, Frankfurt/Main, Nov. 22, 2004, Schulz.
Biotest half-year report of Aug. 11, 2015—Biotest increase revenues in first half year 2015 by 8.9%, pp. 1-3.
Merck Manual of Diagnosis and Therapy, Merck Research Laboratories, 1999, pp. 940-941, 949-951 and 968-969.
Severin et al., "Biochemistry", textbook M.: Meditsina, 2000, 168 p.; p. 7 in RU with EN translation.
Wijdenes, J., Slides presented during oral presentation in Heidelberg in Aug. 2003.
Wijdenes, J., poster presented at the EULAR conference in Jun. 2005—"A new type of monoclonal antibody to CD4 for the therapy of rheumatoid arthritis (RA)".
Allez et al., "Regulatory T cells: peace keepers in the gut," Inflamm. Bowel Dis. Sep. 2004;10(5):666-76.
Azuma et al., "Human CD4+ CD25+ regulatory T cells suppress NKT cell functions," Cancer Research (2003); 63: 4516-4520.
Biaze et al., "T cell activation, from atopy to asthma: more a paradox than a paradigm," Allergy Sep. 2003; 58(9): 844-853.
Camara et al., "Human CD4+CD25+ regulatory cells have marked and sustained effects on CD8+ T cell activation," Eur. J. Immunol. Dec. 2003; 33: 3473-3483.
Chen et al., "Induction of Autoantigen-Specific Th2 and Tr1 Regulatory T Cells and Modulation of Autoimmune Diabetes," J. Immunol., 2003, 171: 733-744.
Dore et al., "Identification and location on syndecan-1 core protein of the epitopes of B-B2 and B-B4 monoclonal antibodies," FEBS Letters (1998) 426: 67-70.
Ehrenstein et al., "Compromised function of regulatory T cells in rheumatoid arthritis and reversal by anti-TNFalpha therapy," J. Exp. Med. 2004; 200(3): 277-285.
Ellis et al., "Dissociation of autologous and allogeneic mixed lymphocyte reactivity by using a monoclonal antibody specific for human T helper cells," J. Immunol. 1983; 131(5):2323-7.
Furst et al., "Adalimumab, a fully human anti tumor necrosis factor-alpha monoclonal antibody, and concomitant standard antirheumatic therapy for the treatment of rheumatoid arthritis: results of STAR (Safety Trial of Adalimumab in Rheumatoid Arthritis)," J. Rheumatol. Dec. 2003; 30(12):2563-71.
Jonuleit et al., "The regulatory T cell family: distinct subsets and their interrelations," J. Immunol. 2003; 171: 6323-6327.
Keystone et al., "Radiographic, clinical, and functional outcomes of treatment with adalimumab (a human anti-tumor necrosis factor monoclonal antibody) in patients with active rheumatoid arthritis receiving concomitant methotrexate therapy: a randomized, placebo-controlled, 52-week trial," Arthritis Rheum. May 2004; 50(5):1400-11.

(56) References Cited

OTHER PUBLICATIONS

Keystone et al., "Golimumab, a human antibody to tumour necrosis factor-alpha given by monthly subcutaneous injections, in active rheumatoid arthritis despite methotrexate therapy: the GO-FOR-WARD Study," Ann. Rheum. Dis. Jun. 2009;68(6):789-96. Epub Dec. 9, 2008.
Khapalyuk, A. V., "The General Questions of Clinical Pharmacology and Demonstrative Medicine," Minsk, Oformlenie, 2003, 90 p., p. 49, lines 9-11, 25-31.
Klareskog et al., "Therapeutic effect of the combination of etanercept and methotrexate compared with each treatment alone in patients with rheumatoid arthritis: double-blind randomized controlled trial," The Lancet, 2004, 363:675-681.
Korndörfer et al., "Structural Mechanism of Specific Ligand Recognition by Lipocalin Tailored for the Complexation of Digoxigenin," J. Mol. Biol., Jul. 4, 2003; 330, 385-396.
Krueger et al., "A Randomized, double-blind, placebo-controlled phase III study evaluating efficacy and tolerability of 2 courses of alefacept in patients with chronic plaque psoriasis," J. Am. Acad. Dermatol. 2002; 47:821-33.
Kuritzkes et al., "Antiretroviral Activity of the Anti-CD4 Monoclonal Antibody TNX-355 in Patients Infected with HIV Type 1," J. Infect. Dis. 2004; 189:286-91.
Ling et al., "Relation of CD4+CD25+ regulatory T-cell suppression of allergen-driven T-cell activation to atopic status and expression of allergic disease," Lancet (2004) 363: 608-15.
Maloy et al., "CD4+CD25+ TR cells suppress innate immune pathology through cytokine-dependent mechanisms," J. Exp. Med. (2003); 197(1): 111-119.
Moore et al., "A monoclonal antibody to CD4 domain 2 blocks soluble CD4-induced conformational changes in the envelope glycoproteins of human immunodeficiency virus type 1 (HIV-1) and HIV-1 infection of CD4+ cells," Journal of Virology, 1992, 66(8), 4784-4793.
Morgan et al., "CD25+ cell depletion hastens the onset of severe disease in collagen-induced arthritis," Arthritis and Rheumatism, 2003, 48 (5): 1452-1460.
Mottet et al., "Cutting Edge: Cure of Colitis by CD4+CD25+ Regulatory T Cells," J. Immunol. (2003); 170: 3939-3943.
Ohlson et al., "Detection and characterization of weak affinity antibody antigen recognition with biomolecular interaction analysis," J. Mol. Recognit. May-Jun. 1997; 10(3): 135-8.
Pakula et al., "Genetic analysis of protein stability and function," Annu. Rev. Genet., 1989; 23, 289-310, p. 289 & 306.
Salemi et al., "HIVgp120 activates autoreactive CD4-specific T cell responses by unveiling of hidden CD4 peptides during processing," Journal of Experimental Medicine, 1995, vol. 181 pp. 2253-2257.
Spalding et al., "Cost Effectiveness of Tumor Necrosis Factor-α Inhibitors as First-Line Agents in Rheumatoid Arthritis," Pharmacoeconomics 2006; 24(12): 1221-1232.
Tamura et al., "Structural correlates of an anticarcinoma antibody: Identification of specificity-determining residues (SDRs) and development of a minimally immunogenic antibody variant by retention of SDRs only," The Journal of Immunology, 2000, 164: 1432-1441.
van de Putte et al., "Efficacy and safety of the fully human anti-tumour necrosis factor α monoclonal antibody adalimumab (D2E7) in DMARD refractory patients with rheumatoid arthritis: a 12 week, phase II study," Ann. Rheum. Dis. 2003; vol. 62: 1168-1177.
van de Putte et al., "Efficacy and safety of adalimumab as monotherapy in patients with rheumatoid arthritis for whom previous disease modifying antirheumatic drug treatment has failed," Ann. Rheum. Dis. 2004; vol. 63: 508-516.
Vogt et al., "Construction of an Artificial Receptor Protein ("Anticalin") Based on the Human Apolipoprotein D," ChemBioChem 5, 2004, 191-199.
Wailoo et al., "Technology Assessment: Modeling the cost effectiveness of etanercept, adalimumab and anakinra compared to infliximab in the treatment of patients with rheumatoid arthritis in the medicare program," Agency of Healthcare Research and Quality, 540 Gaither Road, Rockville, Maryland 20850, Oct. 12, 2006.
Wang, W., "Oral protein drug delivery," Journal of Drug Targeting, 1996, vol. 4, No. 4, pp. 195-232.
Wessels et al., "Recent insights in the pharmacological actions of methotrexate in the treatment of rheumatoid arthritis," Rheumatology (Oxford). Mar. 2008;47(3):249-55. Epub Nov. 28, 2007.
Williams et al., "Synergy between anti-CD4 and anti-tumor necrosis factor in the amelioration of established collagen-induced arthritis," PNAS (1994); 91: 2762-2766.
Mima et al., Transfer of rheumatoid arthritis into severe combined immunodeficient mice. The pathogenic implications of T cell populations oligoclonally expanding in the rheumatoid joints. J Clin Invest; 96:1746-1758, 1995.
Moebius et al., Human immunodeficiency virus gp120 binding C'C' ridge of CD4 domain 1 is also involved in interaction with class II major histocompatibility comlex molecules, PNAS USA 89, 12008-120012 (1992)).
Moebius et al., The Human Immunodeficiency Virus gp120 Binding Site on CD4: Delineation by Quantitative Equilibrium and Kinetic Binding Studies of Mutants in Conjunction with a High-Resolution CD4 Atomic Structure, J. Exp. Med. 176, 507-517 (1992)).
Moebius et al., Delination of an extended surface contact area on human CD4 involved in class II major histocompatibility complex binding, Proc. Natl. Acad. Sci. USA 90, 8259-8263 (1993).
Moore and Stevenson, New Targets for Inhibitors of HIV-1 Replication, Nature Rev. Mol. Cell Biol. 1, 40-49 (2000).
Morel et al., Down-regulation of lymphocyte CD4 antigen expression by administration of anti-CD4 monoclonal antibody. Clin. Immunol. Immunopath. 1992; 64(3): 248-253.
Mosteller RD: Simplified Calculation of Body Surface Area. N Engl J Med Oct. 22, 1987;317(17):1098.
Mourad et al., Humanized IgG1 and IgG4 anti-CD4 monoclonal antibodies: Effects on Lymphocytes in the Blood, Lymph Nodes, and Renal Allografts in Cynomolgus Monkeys1. Transplantation 65(5): 632-41 (1998).
Myszka et al., Energetics of the HIV gp120-CD4 binding reaction, Proc. Natl. Acad. Sci. USA 97, 9026-9031 (2000).
Nakamura et al., Cell contact-dependent immunosuppression by CD4(+)CD25(+) regulatory T cells is mediated by cell surface-bound transforming growth factor beta. J Exp. Med. 194: 629-644 (2001).
Nakatani et al., "Functional Expression of Human Monoclonal Antibody Genes Directed Against Pseudomonal Exotoxin A in Mouse Myeloma Cells" Biotechnology 1989; 7: 805-810.
Piatier-Tonneau et al., Characterization of 18 workshop anti-CD4 mAb: epitope mapping to CD4 mutants and effects on CD4-HLA class II interaction. Leucocyte Typing V: White Cell Differentiation Antigens. Proceedings of the 5th Int. Workshop and Conference. Boston, USA Nov. 1993. vol. 1: T39.6: 476-478. Ed. Schlossman et al., OUP 1995.
Piccirillo et al., Cutting edge: control of CD8+ T cell activation by CD4+CD25+ immunoregulatory cells. J. Immunol. 2001; 167: 1137-1140.
Pollock et al., Identification of mutant monoclonal antibodies with increase antigen binding, PNAS 1988; 85: 2298-2302.
Pontoux et al., Natural CD4 CD25+ regulatory T cells control the burst of superantigen-induced cytokine production: the role of IL-10, Int. Immunol. 2002; 14(2) :233-239.
Raja et al., CD4 Binding Site Antibodies Inhibit Human Immunodeficiency Virus gp120 Envelope Glycoprotein Interaction with CCR5, J. Virology Jan. 2003; 77, 713-718.
Rau et al., Adalimumab (a fully human anti-tumour necrosis factor α monoclonal antibody) in the treatment of active rheumatoid arthritis: the initial results of five trials. Ann Rheum Dis 2002; 61(Suppl II): ii70-ii73.
Ravetch and Kinet Fc receptors. Annu Rev Immunol 1991. 9: 457.
Raziuddin et al., (1990), Increased circulating HLA-Dr+ CD4+ T cells in systemic lupus erythematosus: alterations associated with prednisolone therapy. Scand J Immunol.31, 139-45.
Read et al., Cytotoxic T Lymphocyte-Associated Antigen 4 Plays an Essential Role in the Function of Cd25+Cd4+ Regulatory Cells That Control Intestinal Inflammation. J Exp. Med. 192: 295-302 (2000).

(56) References Cited

OTHER PUBLICATIONS

Reinerz and Schlossman, The differentiation and function of human T lymphocytes. Cell 19, 821-827 (1980).
Reinerz et al., Discrete stages of human intrathymic differentiation: Analysis of normal thymocytes and leukemic lymphoblasts of T-cell lineage, PNAS USA 77, 1588-1592 (1980)).
Rizova et al., The effect of anti-CD4 monoclonal antibody treatment on immunopathological changes in psoriatic skin. J Dermatolog. Sci. 1994; 7: 1-13.
Roberts and Szostak, RNA-peptide fusions for the in vitro selection of peptides and proteins. PNAS (1997) 94(23):12297-302).
Robertson and Ritz (1990), Biology and clinical relevance of human natural killer cells. Blood. 76: 2421-38.
Rudd et al., The CD4 receptor is complexed in detergent lysates to a protein-tyrosine kinase (pp58) from human T-lymphocytes, PNAS USA 85, 5190-5194 (1988).
Rumbach et al., Essai thérapeutique ouvert d'un anticorps monoclonal anti-T CD4 dans la sclérose en plaques. Rev. Neurol. (Paris) 1994; 150 (6-7): 418-424.
Rump et al., A double blind, placebo-controlled, crossover therapy study with natural human IL-2 (nhuIL-2) in combination with regular intravenous gammaglobulin (IVIG) infusions in 10 patients with common variable immunodeficiency (CVID). Clin. Exp. Immunol. 1997; 110:167-173.
Sakaguchi et al., Immunologic tolerance maintained by CD25+ CD4+ regulatory T cells: their common role in controlling autoimmunity, tumor immunity, and transplantation tolerance. Immunol. Rev. 182: 18-32 (2001).
Salomon et al., B7/CD28 costimulation is essential for the homeostasis of the CD4+CD25+ immunoregulatory T cells that control autoimmune diabetes. Immunity 12: 431-440 (2000).
Sany J. Immunological treatment of rheumatoid arthritis. Clin Exp. Rheumatol; 8 (Suppl 5): 81-88, 1990.
Sattentau et al., Epitopes of CD4 antigen and HIV infection. Science 1986. 234: 1120.
Sattentau et al., Structural Analysis of the Human Immunodeficiency Virus-Binding Domain of CD4, J. Exp. Med. 170, 1319-1334 (1989).
Seddon and Mason, Peripheral Autoantigen induces regulatory T cells that prevent autoimmunity. J. Exp. Med. 189 (5): 877-881, 1999.
Shevach, Regulatory T cells in autoimmunity. Annu. Rev. Immunol. 18: 423-449 (2000).
Shevach, CD4+CD25+ suppressor T cells: more questions than answers. Nature Rev. Immunol 2 : 389 (2002).
Simon et al., A Rat CD4 Mutant Containing the gp120-binding Site Mediates Human Immunodeficiency Virus Type 1 Infection, J. Exp. Med. 177, 949-954 (1993).
Smeets et al., Poor expression of T cell derived cytokines and activation and proliferation markers in early rheumatoid synovial tissue. Clin. Immunol. Immunopathol. 88: 84-90, 1998.
Soundararajan et al., Clinical and immunological effects of a primatized anti CD4 antibody used concomitantly with methotrexate in rheumatoid arthritis. J. Allergy & Clin. Immunol. 1997; 99 No. 1 Pt. 2: S193 No. 777.
Stein et al., Immunohistological analysis of human lymphoma: correlation of histological and immunological categories. Adv Cancer Res. 1984;42:67-147.
Suri-Payer et al., Pathogenesis of post-thymectomy autoimmune gastritis. Identification of anti-H/K adenosine triphosphatase-reactive T cells. J Immunol. 157: 1799-1805 (1996).
Suri-Payer et al., CD4+CD25+ T cells inhibit both the induction and effector function of autoreactive T cells and represent a unique lineage of immunoregulatory cells. J. Immunol. 160: 1212-1218 (1998).
Suto et al., Role of CD4+CD25+ regulatory T cells in T helper 2 cell-mediated allergic inflammation in the airways. Am. J. Respir. Crit. Care Med. 2001; 164: 680-687.
Tamm et al., IgG binding sites on human Fcgamma receptors. Intern. Rev. Immunol. 1997; 16: 57-85.
Thornton and Shevach, CD4+CD25+ immunoregulatory T cell suppress polyclonal T cell activation in vitro by inhibiting interleukin-2 production, J. Exp. Med. 1998; 188(2): 287-96.
Tifft et al., The Folding and Cell Surface Expression of CD4 Requires Glycosylation, J. Biol. Chem. 267, 3268-3273 (1992).
Tribbick et al., Multipin peptide libraries for antibody and receptor epitope screening and characterization. J Immunl. Methods (2002) 267: 27-35).
Trickett et al, T cell stimulation and expansion using anti-CD3/ CD28 beads, J. Immunol. Methods, 2003; 275: 251-255.
Tuosto et al., Differential susceptibility of monomeric HIV gp120-mediateds apoptosis in antigen-activated CD4+ T cell populations, Eur. J. Immunol. 25, 2907-2916 (1995).
Veillette et al., The CD4 and CD8 T cell surface antigens are associated with the internal membrane tyrosine-protein kinase p56lck, Cell 55, 301 (1988)).
Wang et al., Crystal structure of the human CD4 N-terminal two-domain fragment complexed to a class II MHC molecule, Proc. Natl. Acad. Sci. USA 98, 10799-10804 (2001).
Wascher et al., Cell-type specific response of peripheral blood lymphocytes to methotrexate in the treatment of rheumatoid arthritis. Clin Investig. Jul. 1994;72(7):535-40.
Wendling et al., Therapeutic use of monoclonal anti-CD4 antibody in rheumatoid arthritis. J Rheumatol 18, 325-327, 1991.
Wendling et al., Combination therapy of anti-CD4 and anti-IL6 monoclonal antibodies in a case of severe spondylarthropathy, British J. of Rheumatol, 1998; 35(12): 1130.
Wijdenes et al., Monoclonal antibodies in human organ transplantation and auto-immune disease. Therapie 1992; 47: 283-7.
Willerford et al., Interleukin-2 receptor alpha chain regulates the size and content of the peripheral lymphoid compartment. Immunity 3: 521-530 (1995).
Willkommen and Löwer. Theoretical considerations on viral inactivation or elimination. Brown F (ed): Virological Safety Aspects of Plasma Derivatives Dev Biol Stand. Basel, Karger 1993, vol. 81: 109-116.
Baecher-Allan, C., et al., "Functional analysis of highly defined, FACS-isolated populations of human regulatory CD4+CD25+ T cells," Clin. Immunol. 2005;115:10-18.
Fuss, I. J. et al. "Nonclassical CD1d-restricted NK T cells that produce IL-13 characterize an atypical Th2 response in ulcerative colitis," J. Clin. Investigation 2004;113(10):1490-1497.
Glamann, J., et al., "Characterization of a Macaque Recombinant Monoclonal Antibody That Binds to a CD4-Induced Epitope and Neutralizes Simian Immunodeficiency Virus," J. Virol. 2000;74(15):7158-7163.
Godfrey, D. I., et al., "NKT cells: facts, functions and fallacies," Immunology Today 2000;21(11):573-583.
The Biotest AG Company Presentation dated Jan. 2008, pp. 1-33.
Colman, P. M., "Effects of amino acid sequence changes on antibody-antigen interactions," Res. In Immunol. 1994;145:33-36.
Cronstein, B. N., "Low-Dose Methotrexate: A Mainstay in the Treatment of Rheumatoid Arthritis," Pharmacol. Rev. 2005;57(2):163-173.
Karim, M., et al., "CD25+CD4+ regulatory T cells generated by exposure to a model protein antigen prevent allograft rejection: antigen-specific reactivation in vivo is critical for bystander regulation," Blood 2005;105(12):4871-4877.
Lack, J.A., et al., "Calculation of drug dosage and body surface area of children," Br. J. Anaesth. 1997;78(5):601-605.
Lorenz, H.-M., et al., "Biological Agents in Rheumatoid Arthritis Which Ones Could Be Used in Combination?" BioDrugs 1998;9(4):303-324.
Pincus, T., et al., "Methotrexate as the "anchor drug" for the treatment of early rheumatoid arthritis," Clin. Exp. Rheumatol. 2003;21(Suppl. 31):S179-S185.
Rudikoff, S., et al., "Single amino acid substitution altering antigen-binding specificity," Proc. Natl. Acad. Sci USA 1982;79:1979-1983.
Strom, T. B., et al., "Therapeutic Approach to Organ Transplantation," Therapeutic Immunology, edited by Austen et al., Blackwell Science, Cambridge, MA 1996; pp. 451-456.

(56) References Cited

OTHER PUBLICATIONS

Wijdenes, J., et al., "A New Type of Monoclonal Antibody to CD4 for the Therapy of Rheumatoid Arthritis (RA)," Ann. Rheum. Dis. 2005;64(Suppl. III):444 (Abstract)/.
Baecher-Allan et al., J. Immunol. Dec. 1, 2002;169(11):6210-6217.
Office Action issued in co-pending U.S. Appl. No. 12/880,837 (Mar. 22, 2012).
Office Action issued in co-pending U.S. Appl. No. 12/880,768 (Mar. 22, 2012).
Office Action issued in co-pending U.S. Appl. No. 12/880,623 (Mar. 22, 2012).
Office Action issued in co-pending U.S. Appl. No. 13/074,357 (Mar. 22, 2012).
Anderson, D., et al., "A Primatized1 MAb to Human CD4 Causes Receptor Modulation, without Marked Reduction in CD4+ T Cells in Chimpanzees: In Vitro and in Vivo Characterization of a MAb (IDEC-CE9.1) to Human CD4," Clin. Immunol. Immunopath. 1997;84(1):73-84.
Apostolou, I., et al., "Origin of regulatory T cells with known specificity for antigen," Nat. Immunol. 2002;3 (8):756-763.
Balandina, A., et al., "Analysis of CD4+CD25+ Cell Population in the Thymus from Myasthenia Gravis Patients," Ann. NY Acad. Sci. 2003;998:275-277.
Bennett, C. L., et al., "The immune dysregulation, polyendocrinopathy, enteropathy, X-linked syndrome (IPEX) is caused by mutations of FOXP3," Nat. Genet. 2001;27:20-21.
Brooks, P., et al., "Outcome measures and classification criteria for the rheumatic diseases. A compilation of data from OMERACT (Outcome Measures for Arthritis Clinical Trials), ILAR (International League of Associations for Rheumatology), regional leagues and other groups," Rheumatol. 2001;40:896-906.
Felson, D. T., et al., "The American College of Rheumatology Preliminary Core Set of Disease Activity Measures for Rheumatoid Arthritis Clinical Trials," Arthritis Rheum. 1993;36(6):729-740.
Fontenot, J. D., et al., "Foxp3 programs the development and function of CD4+CD25+ regulatory T cells," Nat. Immunol. 2003;4(4):330-336.
Grynkiewicz, G., et al., "A New Generation of Ca2+ Indicators with Greatly Improved Fluorescence Properties," J. Biol. Chem. 1985;260(6):3440-3450.
Hori, S., et al., "Control of Regulatory T Cell Development by the Transcription Factor Foxp3," Science 2003;299:1057-1061.
Lin, C.-H., et al., "Efficient expansion of regulatory T cells in vitro and in vivo with a CD28 superagonist," Eur. J. Immunol. 2003;33:626-638.
Lipsky, P. E., et al., "Infliximab and Methotrexate in the Treatment of Rheumatoid Arthritis," N. Engl. J. Med. 2000;343:1594-1602.
Newsome, G., et al., "Guidelines for the Management of Rheumatoid Arthritis: 2002 Update," J. Am. Acad. Nurse Prac. 2002;14(10):432-437.
Prevoo, M. L. I., et al., "Modified Disease Activity Scores That Include Twenty-Eight-Joint Counts," Arthritis Rheum. 1995;38(1):44-48.
Reddy, M. P., et al., "Elimination of Fc Receptor-Dependent Effector Functions of a Modified IgG4 Monoclonal Antibody to Human CD4," J. Immunol. 2000;164:1925-1933.
Smolen, J. S., et al., "Validity and Reliability of the Twenty-Eight-Joint Count for the Assessment of Rheumatoid Arthritis Activity," Arthritis Rheum. 1995;38(1):38-43.
Goolsby, M. J., et al., "Guidelines for the Management of Rheumatoid Arthritis 2002 Update," J. Am. Acad. Nurse Practitioners 2002;14(10):432-437.
Ansel, et al., Pharmaceutical Dosage Forms and Drug Delivery Systems, Lippincott Williams & Wilkens, Philadelphia, PA, 1999; 126-127.
Roitt, A., et al., Extract from Chapter 6, Immunology (2000), Moscow, "Mir", pp. 110-111 and English translation of section bridging pp. 110-111.
Riechmann, L., et al., "Reshaping human antibodies for therapy," Nature 1988;332:323-327.

JF Bach, Nat. Rev. Immunol. Mar. 2003;3(3):189-198.
Pohlers et al., Arthritis Res. 2002, 4:184-189.
Wendling, D., et al., "Treatment of Rheumatoid Arthritis with Anti CD4 Monoclonal Antibody. Open Study of 25 Patients with the B-F5 Clone," Clin. Rheumatol. 1992;11(4):542-547.
Wendling, D., et al., "A Randomized, Double Blind, Placebo Controlled Multicenter Trial of Murine Anti-CD4 Monoclonal Antibody Therapy in Rheumatoid Arthritis," J. Rheumatol. 1998;25(8):1457-1461.
Zhu, Z., et al., "Inhibition of human leukemia in an animal model with human antibodies directed against vascular endothelial growth factor 2. Correlation between antibody affinity and biological activity," Leukemia 2003;17:604-611.
Bartholomew, M., et al., "Functional analysis of the effects of a fully humanized anti-CD4 antibody on resting and activated human T cells," Immunology 1995;85(1):41-48.
Racadot, E., et al., "Immunological follow-up of 17 patients with rheumatoid arthritis treated in vivo with an anti-T CD4+ monoclonal antibody (B-F5)," Clin. Exp. Rheumatol. 1992;10:365-374.
Panka, et al., "Variable region framework differences result in decreased or increased affinity of variant anti-digoxin antibodies," Proc. Natl. Acad. Sci. 1988;85:3080-3084.
Rudikoff et al., "Single amino substitution altering antigen-binding specificity," Proc. Natl. Acad. Aci. 1982;79:1979-1983.
International Search Report for PCT/EP2004/002888 (Aug. 5, 2004).
International Preliminary Examination Report for PCT/EP2004/002888 (Jan. 12, 2005).
Choy, E. H. S., et al., "Percentage of Anti-CD4 Monoclonal Antibody-Coated Lymphocytes in the Rheumatoid Joint is Associated With Clinical Improvement," Arthritis & Rheumatism 1996;39(1):52-56.
Horneff, G., et al., "Treatment of Rheumatoid Arthritis With an Anti-CD4 Monoclonal Antibody," Arthritis & Rheumatism 1991;34(2):129-140.
Isaacs, J. D., et al., "Humanized Anti-CD4 Monoclonal Antibody Therapy of Autoimmune and Inflammatory Disease," Clin. Exp. Immunol. 1997;110:158-166.
Reiter, C., et al., "Treatment of Rheumatoid Arthritis With Monoclonal CD4 Antibody M-T151," Arthritis & Rheumatism 1991;34(5):525-536.
Robinet, E., et al., "Clinical Improvement of a Patient With Severe Psoriasis Following CD4 Antibody Administration Despite a Blocking Antibody-Host Response," Eur. J. Dermatol. 1996;6:141-146.
Robinet, E., et al., "CD4 Monoclonal Antibody Administration in Atopic Dermatitis," J. Amer. Acad. Dermatol. 1997;36(4):582-588.
Takahashi, N., et al., "Structure of Human Immunoglobulin Gamma Genes: Implication for Evolution of a Gene Family," Cell 1982;29:671-679.
Van Der Lubbe, P. A., et al., "Chimeric CD4 Monoclonal Antibody cM-T412 as a Therapeutic Approach to Rheumatoid Arthritis," Arthritis & Rheumatism 1993;36(10):1375-1379.
Baca, M., et al., "Antibody Humanization Using Monovalent Phage Display," J. Biol. Chem. 1997;272(16):10678-10684.
Becker, C., et al., "CD4-mediated functional activation of human CD4+CD25+ regulatory T cells," Eur. J. Immunol. 2007;37:1217-1223.
Chapman, A. P., et al., "Therapeutic antibody fragments with prolonged in vivo half-lives," Nature Biotechnol. 1999;17:780-783.
Fournel, S., et al., "Clonal deletion and clonal anergy mediated by antibodies to the human CD4 protein," pp. 255-264 from Rejection and tolerance: proceedings of the 25th Conference on Transplantation and Clinical Immunology, published by Springer, 1994.
Humphreys, D. P., et al., "F(ab')2 molecules made from *Escherichia coli* produced Fab' with hinge sequences conferring increased serum survival in animal model," J. Immunol. Methods 1998;217:1-10.
Morel, P., et al., "Internalization and Degradation of Anti-CD4 Monoclonal Antibodies Bound to Human Peripheral Blood Lymphocytes," Mol. Immunol. 1993;30(7):649-657.
Racadot, E., et al., "Immunological follow-up of 17 patients with rheumatoid arthritis treated in vivo with an anti-CD4+ monoclonal antibody (B-F5)," Clin. Experimen. Rheumatol. 1992;10:365-374.

(56) References Cited

OTHER PUBLICATIONS

Sakaguchi, S., et al., "Immunologic tolerance maintained by CD25+ CD4+ regulatory T cells: their common role in controlling autoimmunity, tumor immunity, and transplantation tolerance," Immunol. Rev. 2001;182:18-32.

Casset, F., et al., "A peptide mimetic of an anti-CD4 monoclonal antibody by rational design," Biochem Biophys. Res. Comm. 2003;307:198-205.

Choy, E. H. S., et al., "Anti-CD4 monoclonal antibodies in rheumatoid arthritis," Springer Semin. Immunopathol. 1998;20:261-273.

Skerra, A., "Engineered protein scaffolds for molecular recognition," J. Mol. Recognit. 2000;13:167-187.

Choy, E. H. S., et al., "Chimaeric anti-CD4 monoclonal antibody cross-linked by monocyte Fcγ receptor mediates apoptosis of human CD4 lymphocytes," Eur. J. Immunol. 1993;23:2676-2681.

Kingsley, C. I., et al., "CD25+CD4+ Regulatory T Cells Prevent Graft Rejection: CTLA-4- and IL-10-Dependent Immunoregulation of Alloresponses," J. Immunol. 2002;168:1080-1086.

Mizukami, T., et al., "Binding region for human immunodeficiency virus (HIV) and epitopes for HIV-blocking monoclonal antibodies of the CD4 molecule defined by site-directed mutagenesis," Proc. Natl. Acad. Sci. USA 1988; 85:9273-9277.

Kim, J. M., et al., "When Does Rheumatoid Arthritis Begin and Why Do We Need to Know?" Arthritis & Rheumatism 2000;43(3):473-484.

Kraan, M. C., et al., "Asymptomatic Synovitis Precedes Clinically Manifest Arthritis," Arthritis & Rheumatism 1998;41 (8):1481-1488.

Schulze-Koops, H., et al., "Reduction of Th1 Cell Activity in the Peripheral Circulation of Patients with Rheumatoid Arthritis After Treatment with a Non-Depleting Humanized Monoclonal Antibody to CD4," J. Rheumatol. 1998;25 (11):2065-2076.

Webster's New World Dictionary, Third College Edition, 1988, pp. 1067-1068.

Abramowicz et al., Release of tumor necrosis factor, interleukin-2, and gamma-interferon in serum after injection of OKT3 monoclonal antibody in kidney transplant recipients. Transplantation. Apr. 1989;47(4):606-8.

Abramowicz et al, Anaphylactic shock after retreatment with OKT3 monoclonal antibody. N Engl. J Med. Sep. 3, 1992;327(10):736.

Anderson et al., (1983) Antigens on human plasma cells identified by monoclonal antibodies. J Immunol. 130:1132-8.

Asano et al., Autoimmune disease as a consequence of developmental abnormality of a T cell subpopulation. J Exp. Med. 184:387-396 (1996).

Ashkenazi et al., Mapping the CD4 binding site for human immunodefincinecy virus by alanine-scanning mutagenesis, PNAS USA 87, 7150-7154 (1990)).

Bachelez et al., Treatment of recalcitrant plaque psoriasis with a humanized non-depleting antibody to CD4. J. Autoimmunity 1998; 11: 53-62.

Beste et al., Small antibody-like proteins with prescribed ligand specificities derived from the lipocalin fold, Proc. Natl. Acad. Sci. USA 96, 1898-1903 (1999).

Bone and Handy, Ab initio studies of internal rotation barriers and vibrational frequencies of (C2H2)2, (CO2)2, and C2H2—CO2, Theor. Chim. Acta 78, 133-163 (1990).

Bonomo et al., Pathogenesis of post-thymectomy autoimmunity. Role of syngeneic MLR-reactive T cells. J. Immunol. 154: 6602-6611 (1995).

Briand et al., Application and limitations of the multi antigen peptide (MAP) system in the production and evaluation of antipeptide and anti-protein antibodies. J Immunol Methods (1992). 156; 2: pp. 255-265).

Cammarota et al., Identification of a CD4 binding site on the beta2 domain of HLA-DR molecules, Nature 356, 799-801 (1992).

Cao and Leroux-Roels Antigen-specific T cell responses in human peripheral blood leucocyte (hu-PBL)-mouse chimera conditioned with radiation and an antibody directed against the mouse IL-2 receptor beta-chain.Clin. Exp. Immunol. Oct. 2000;122(1): 117-123.

Cao et al., Isolation and functional characterisation of regulatory CD25brightCD4+ T cells from the target organ of patients with rheumatoid arthritis. Eur J Immunol, 33: 215-223, 2003.

Carr et al., Protein and carbohydrate structural analysis of a recombinant soluble CD4 receptor by mass spectrometry, J. Biol. Chem. 264, 21286-21295 (1989).

Carriere et al., "CD4 Masking during Human Immunodeficiency Virus Type 1 Infection, Quantified on Peripheral Blood Lymphocytes, Is a Potential Marker of Disease Progression" J. Inf. Dis. 1996;173: 565-73.

Carter et al., Humanization of an anti-p185HER2 antibody for human cancer therapy, Proc. Natl. Acad. Sci. USA 89, 4285-4289 (1992).

Chen et al., Regulatory T cell clones induced by oral tolerance: suppression of autoimmune encephalomyelitis. Science 265:1237-1240 (1994).

Choy et al., Monoclonal antibody therapy in rheumatoid arthritis, B. J. Rheumatol. 1998;37: 484-490.

Choy et al., Pharmacokinetic, pharmacodynamic and clinical effects of a humanized IgG1 anti-CD4 monoclonal antibody in the peripheral blood and synovial fluid of rheumatoid arthritis. Rheumatology 39(10): 1139-46 (2000).

Choy et al., Repeat-cycle study of high-dose intravenous 4162W94 anti-CD4 humanized monoclonal antibody in rheumatoid arthritis. A randomized placebo-controlled trial. Rheumatology 41 (10):1142-8 (2002).

Choy et al., Efficacy of a novel PEGylated humanized anti-TNF fragment (CDP870) in patients with rheumatoid arthritis: a phase II double-blinded, randomized, dose-escalating trial. Rheumatology 2002; 41: 1133-1137.

Dowd et al., β-Turn Phe in HIV-1 Env Binding Site of CD4 and CD4 Mimetic Miniprotein Enhances Env Binding Affinity but is Not Required for Activation of Co-Receptor/17b Site, Biochemistry 41, 7038-7046 (2002).

DuBois D; DuBois EF: A formula to estimate the approximate surface area if height and weight be known. Arch Int Med 1916 17:863-71.

Felson et al., Preliminary definition of improvement in rheumatoid arthritis. Arthritis & Rheumatism, 1995, 38(6), 727-735.

Fitch, T-cell clones and T-cell receptors, Microbiol. Rev. 50, 50-69 (1986).

Froebel et al., 1999. Standardization and quality assurance of lymphocyte proliferation assays for use in the assessment of immune function. J. Immunol. Methods 227: 85-97.

Gehan EA, George SL, Estimation of human body surface area from height and weight. Cancer Chemother Rep 1970 54:225-35.

Gellman, Foldamers: A Manifesto. Acc. Chem. Res (1998) 31 (4): 173-180.

Gessner et al., The IgG Fc receptor family. Ann Hematol 1998. 76: 231.

Gorelik and Flavell, Abrogation of TGFβ signaling in T cells leads to spontaneous T cell differentiation and autoimmune disease. Immunity 12: 171-181, 2000.

Gottlieb et al., Anti-CD4 monoclonal antibody treatment of moderate to severe psoriasis vulgaris: Results of a pilot, multicenter, multiple-dose, placebo-controlled study. Acad Dermatol 2000; 43 : 595-604.

Göttlinger et al., Vpu protein of human immunodeficiency virus type 1 enhances the release of capsids produced by gag gene constructs of widely divergent retroviruses, Proc. Natl. Acad. Sci. USA 90, 7381-7385 (1993).

Gray et al., (1994), The role of transforming growth factor beta in the generation of suppression: an interaction between CD8+ T and NK cells. J Exp Med. 180:1937-42.

Hammond et al., Antigenic Variation within the CD4 Binding Site of Human Immunodeficiency Virus Type 1 gp120: Effects on Chemokine Receptor Utilization, J. Virology 75, 5593-5603 (2001).

Hara et al., (2001), IL-10 is required for regulatory T cells to mediate tolerance to alloantigens in vivo. J Immunol. 166:3789-96.

(56) References Cited

OTHER PUBLICATIONS

Haycock G.B., Schwartz G.J., Wisotsky D.H. Geometric method for measuring body surface area: A height weight formula validated in infants, children and adults. The Journal of Pediatrics 1978 93:1:62-66.

Hepburn et al., Antibody-mediated stripping of CD4 from lymphocyte cell surface in patients with rheumatoid arthritis. Rheumatology Jan. 2003 ;42(1): 54-61.

Herold et al., Anti-CD3 monoclonal antibody in new-onset Type 1 Disease Mellitus. N. Engl. J. Med. 2002; 346(22): 1692-1698.

Herzyk et al., Immunomodulatory Effects of Anti-CD4 Antibody in Host Resistance against Infections and Tumors in Human CD4 Transgenic Mice. Infect Immun. 69(2): 1032-43 (2001).

Hill et al., A Field Guide to Foldamers. Chem. Rev. (2001) 101 (12): 3893-4012.

Horwitz et al., (1999), Role of NK cells and TGF-beta in the regulation of T-cell-dependent antibody production in health and autoimmune disease. Microbes Infect. 1:1305-11.

Howie et al., Synthetic peptides representing discontinuous CD4 binding epitopes of HIV-1 gp120 that induce T cell apoptosis and block cell death induced by gp120, FASEB J. 12, 991-998 (1998).

Isaacs et al., A therapeutic human IgG4 monoclonal antibody that depletes target cells in humans, Clin. Exp. Immunol. 1996; 106: 427-433.

Jabado et al., CD4 ligands inhibit the formation of multifunctional transduction complexes involved in T cell activation. J Immunol. 158(1): 94-103 (1997)).

Jameson et al., Location and Chemical Synthesis of a Binding Site for HIV-1 on the CD4 Protein, Science 240, 1335-1339 (1988).

Jefferis and Lund, Interaction sites on human IgG-Fc for Fcγ: current models. Immunol. Lett. 2002;82: 57.

Kingsley et al., Immunogenetic and cellular immune mechanism in rheumatoid arthritis: relevance to new therapeutic strategies. Br J Rheumatol, 29, 58-64, 1990.

Kipps et al., Importance of immunoglobulin isotype in human antibody-dependent, cell-mediated cytotoxicity directed by murine monoclonal antibodies, J. Exp. Med. 1985; 161: 1-17.

Kon et al., Randomised, dose-ranging , placebo-controlled study of chimeric antibody to CD4 (keliximab) in chronic severe asthma, Lancet Oct. 3, 1998; 352 (9134):1109-13.

Kon et al., The effects of an anti-CD4 monoclonal antibody, keliximab, on peripheral blood CD4zT-cells in asthma. Eur Respir J. 18(1): 45-52 (2001).

König et al., Glycosylation of CD4. J. Biol. Chem. 263, 9502-9507 (1988).

Kwong et al., Structure of an HIV gp120 envelope glycoprotein in complex with the CD4 receptor and a neutralizing human antibody, Nature 393, 648-659 (1998).

Lam TK, Leung DT: More on simplified calculation of body-surface area. N Engl J Med Apr. 28, 1988;318(17):1130.

Lamarre et al., The MHC-Binding and gp120-Binding Functions of CD4 Are Separable, Science 245, 743-746 (1989).

Lanza et al., Active immunity against the CD4 receptor by using an antibody antigenized with residues 41-55 of the first extracellular domain, PNAS USA 90, 11683-11687 (1993)).

Lawendowski et al., Solid phase epitope recovery. J Immunol., (2002) 169: 2414-2421).

Luggen et al., Results of a phase II double-blind, randomized study of a nondepleting anti-CD4 monoclonal antibody (Clenoliximab) given in combination with methotrexate (MTX) in patients with moderate to severe rheumatoid arthritis. Annals of Rheum. Dis. 2003; 62(1): 99.

Lusso et al., CD4 is a critical component of the receptor for human herpes virus 7: Interference with human immunodeficiency virus, Proc. Natl. Acad. Sci. USA 91, 3872-3876 (1994).

Maddon et al., The isolation and nucleotide sequence of a cDNA encoding the T cell surface protein T4. Cell. 1985; 42 (1):93-104.

Mason et al., CD4 coating, but not CD4 depletion, is a predictor of efficacy with primatized monoclonal anti-CD4 treatment of active rheumatoid arthritis. J Rheumatol. 29(2): 220-9 (2002).

Mattheakis et al., An in vitro polysome display system for identifying ligands from large peptide libraries. PNAS 1994; 91(19):9022-6).

Mazerolles et al., A synthetic peptide mimicking the HLA-DR β2-binding site for CD4+ T cell adhesion to B cells and CD4+ T cell activation, Int. Immunology 8, 267-274 (1996).

McKeithan, Kinetic proofreading in T-cell receptor signal transduction, PNAS 1995, 92; 5042-5046.

* cited by examiner mB-F5 V$_H$ :

CAG GAA TAC CTT GTG GAG ACC GGG GGA GGC TTG GTG AGG CCT GGA AAT TCT CTG AAA

CTC TCC TGT GTC ACC TCG GGT TTC AGT TTC AGT GAC TGC CGG ATG TAC TGG CTT CGC

CAG CCT CCA GGG AAG GGG CTG GAG TGG ATT GGT GTG ATT TCA GTC AAA TCT GAG AAT

TAT GGA GCA AAT TAT GCA GAG TCT GTG AGG GGC AGA TTC ACT ATT TCA AGA GAT GAT

TCA AAA AGC AGT GTC TAT CTG CAG ATG AGC AGA TTG AGA GAG GAA GAC ACT GCC ACT

TAT TAT TGT AGT GCC TCC TAT TAT AGG TAC GAC GTG GGG GCC TGG TTT GCT TAC TGG

GGC CAA GGG ACT CTG GTC ACT GTC TCT GCA

Figure 1 mB-F5 V_K :

GAC ATT GTG CTG ACA CAG TCT CCT TCT TCC TTA GTT GTA TCT CTG GGG CAG AGG GCC

ACC ATC TCA TGC AGG GCC AGC AAA AGT GTC AGT ACA TCT GGC TAC AGT TAT ATA TAT

TGG TAC CAA CAG ATC CCA GGA CAG CCA CCC AAA CTC CTC ATC TAT CTT GCA TCC ATC

CTA GAA TCT GGG GTC CCT GGC AGG TTC AGT GGC AGT GGG TCT GGG ACA GAC TTC ACC

CTC AAC ATC CAT CCT GTG GAG GAG GAG GAT GCT GCA ACC TAT TAC TGT CAG CAC AGT

AGG GAA CTT CCG TGG ACG TTC GGT GGA GGC ACC AAG CTG GAG ATC AAA CGG GCT GAT

GCT GCA CCA ACT GTA TCC ATC TTC CCA CCA TCC AGT GAG CA

Figure 2

```
            FR1                    CDR1              FR2
             1              2        3               4
    12345678901234567890123 456777778901234 567890123456789
                                ABCD mB-F5      DIMLTQSPSSLVVSLGQRATISC RASKSVSTSGYSYIY WYQQIPGQPPKLLIY
hB-F5L4M   DIVMTQSPDSLAVSLGERATINC RASKSVSTSGYSYIY WYQQKPGQPPKLLIY
hB-F5L4L   --IL-------------------  --------------  ---------------
FK-001     DIVMTQSPDSLAVSLGERATINC                 WYQQKPGQPPKLLIY

CDR2           FR3
             5      6       7          8
            0123456 789012345678901234567890123456678 mB-F5      LASILES GVPGRFSGSGSGTDFTLNIHPVEEEDAATYYC
hB-F5L4M   LASILES GVPDRFSGSGSGTDFTLTISSLQAEDVAVYYC
hB-F5L4L   ------- ---------------------------------
FK-001             GVPDRFSGSGSGTDFTLTISSLQAEDVAVYYC

CDR3      FR4
             9         10
            901234567 8901234567 mB-F5      QHSRELPWT FGGGTKLEIK
hB-F5L4M   QHSRELPWT FGQGTKVEIK
hB-F5L4L   --------- ----------
FK-001               FGQGTKVEIK
```

Figure 3

```
              FR1                            CDR1     FR2
        1         2         3                        4
        12345678901234567890123456789 0 12345 678901234567890
```

```
mB-F5      QEYLVETGGGLVRPGNSLKLSCVTSGFSFS  DCRMY  WLRQPPGKGLEWIG
hB-F5H37V  EVQLVESGGGLVKPGGSLRLSCAASGFSFS  DCRMY  WVRQAPGKGLEWIG
hB-F5H37L  --|-------------------------|-  -----  -L-----------|-
M26        EVQLVESGGGLVKPGGSLRLSCAASGFTFS         WVRQAPGKGLEWVG
```

```
              CDR2                          FR3
         5           6             7         8              9
         0122223456789012345 6789012345678901222234 5678901234
             ABC                                  ABC
```

```
mB-F5       VISVKSENYGANYAESVRG  RFTISRDDSKSSVYLQMSRLREEDTATYYCSA
hB-F5H37V   VISVKSENYGANYAESVRG  RFTISRDDSKNTVYLQMNSLKTEDTAVYYCSA
hB-F5H37L   -------------------  -|---|---|--|-|--------------|-
M26                              RFTISRDDSKNTVYLQMNSLKTEDTAVYYCTT
```

```
         CDR3            FR4
          10             11
     5678900000012  34567890123
          ABCDE
```

```
mB-F5      SYYRYDVGAWFAY   WGQGTLVTVSA
hB-F5H37V  SYYRYDVGAWFAY   WGQGTLVTVSS
hB-F5H37L  -------------   |---------|
M26                        WGQGTLVTVSS
```

Figure 4

```
GA GGA GCT CCA GAC AAT GTC TGT CTC CTT CCT CAT CTT CCT GCC CGT GCT GGG CCT

CCC ATG GGG TCA GTG TCA GGG AGA TGC CGT ATT CAC AGC AGC ATT CAC AGA CTG AGG

GGT GTT TCA CTT TGC TGT TTC CTT TTG TCT CCA GGT GTC CTG TCA GAG GAA CAG CTT
                                                            E   E   Q   L

GTG GAG TCT GGG GGA GGC TTG GTG AAA CCC GGA GGT TCT CTG AGG CTC TCC TGT GCA
 V   E   S   G   G   G   L   V   K   P   G   G   S   L   R   L   S   C   A

GCC TCG GGT TTC AGT TTC AGT GAC TGC CGG ATG TAC TGG GTT CGC CAG GCT CCA GGG
 A   S   G   F   S   F   S   D   C   R   M   Y   W   V   R   Q   A   P   G

AAG GGG CTG GAG TGG ATT GGT GTG ATT TCA GTC AAA TCT GAG AAT TAT GGA GCA AAT
 K   G   L   E   W   I   G   V   I   S   V   K   S   E   N   Y   G   A   N

TAT GCA GAG TCT GTG AGG GGC AGA TTC ACT ATT TCA AGA GAT GAT TCA AAA AAC ACG
 Y   A   E   S   V   R   G   R   F   T   I   S   R   D   D   S   K   N   T

GTC TAT CTG CAG ATG AAC AGC TTG AAG ACC GAA GAC ACT GCC GTT TAT TAT TGT AGT
 V   Y   L   Q   M   N   S   L   K   T   E   D   T   A   V   Y   Y   C   S

GCC TCC TAT TAT AGG TAC GAC GTG GGG GCC TGG TTT GCT TAC TGG GGC CAA GGG ACT
 A   S   Y   Y   R   Y   D   V   G   A   W   F   A   Y   W   G   Q   G   T

CTG GTC ACT GTC TCT TCA GGT AAG AAT GGC CAA GCT TG
 L   V   T   V   S   S
```

Figure 5

```
GGA GGA TCC AAT TAT CTG CTG ACT TAT AAT ACT ACT AGA AAG CAA ATT TAA ATG ACA

TAT TTC AAT TAT ATC TGA GAC AGC GTG TAT AAG TTT ATG TAT AAT CAT TGT CCA TTC

CTG ACT ACA GGT GCC TAC GGG GAC ATC GTG ATG ACC CAG TCT CCA GAC TCC CTG GCT
                                 D   I   V   M   T   Q   S   P   D   S   L   A

GTG TCT CTG GGC GAG AGG GCC ACC ATC AAC TGC AGG GCC AGC AAA AGT GTC AGT ACA
 V   S   L   G   E   R   A   T   I   N   C   R   A   S   K   S   V   S   T

TCT GGC TAC AGT TAT ATA TAT TGG TAC CAG CAG AAA CCA GGA CAG CCT CCT AAG CTG
 S   G   Y   S   Y   I   Y   W   Y   Q   Q   K   P   G   Q   P   P   K   L

CTC ATT TAC CTT GCA TCC ATC CTA GAA TCT GGG GTC CCT GAC CGA TTC AGT GGC AGC
 L   I   Y   L   A   S   I   L   E   S   G   V   P   D   R   F   S   G   S

GGG TCT GGG ACA GAT TTC ACT CTC ACC ATC AGC AGC CTG CAG GCT GAA GAT GTG GCA
 G   S   G   T   D   F   T   L   T   I   S   S   L   Q   A   E   D   V   A

GTT TAT TAC TGT CAG CAC AGT AGG GAA CTT CCG TGG ACG TTC GGC CAA GGG ACC AAG
 V   Y   Y   C   Q   H   S   R   E   L   P   W   T   F   G   Q   G   T   K

GTG GAA ATC AAA CGT GAG TAG AAT TTA AAT TTT AAG CTT CTT
 V   E   I   K
```

Figure 6 ns to tissue antigens:
HUMANIZED ANTI-CD4 ANTIBODY WITH IMMUNOSUPPRESSIVE PROPERTIES This application is a continuation under 35 U.S.C. §120 to U.S. patent application Ser. Nos. 12/392,521 and 12/392,556, which were both filed Feb. 25, 2009, and which are a divisional and continuation, respectively, under 35 U.S.C. §120 to U.S. patent application Ser. No. 12/246,660, filed Oct. 7, 2008, now U.S. Pat. No. 8,586,715, which was a continuation under 35 U.S.C. §120 to U.S. patent application Ser. No. 11/217,402, filed Sep. 2, 2005, now U.S. Pat. No. 7,452,981, which in turn was a continuation under 35 U.S.C. §120 to International application number PCT/EP2004/002888, filed 19 Mar. 2004, which claims priority under 35 U.S.C. §119 to European application no. 03.290725.5, filed 21 Mar. 2003, and European application no. 03.290942.6, filed 16 Apr. 2003, the entireties of which are incorporated by reference herein. The Sequence Listing filed electronically on Jul. 27, 2012 is also hereby incorporated by reference in its entirety (File Name: 2014-02-10T_060-002C4_Seq_List; File Size: 11 KB; Date Created: Feb. 10, 2014).

BACKGROUND OF THE INVENTION

Field of the Invention

The invention relates to a humanized anti-CD4 antibody, and to its use for immunomodulation.

Brief Description of the Related Art

Autoimmune diseases as well as graft rejection result from an inappropriate immune response to tissue antigens: self antigens in the first case, and allograft antigens in the second one.

Autoimmune diseases include for instance rheumatoid arthritis, type I diabetes, multiple sclerosis, Crohn's disease, ulcerative colitis, atopic dermatitis, etc.

Conventional treatments for these immunological disorders involve immunosuppressive drugs. However these drugs induce a general immunosuppression, resulting in inhibition of not only the harmful functions of the immune system, but also the useful ones. As a consequence, they induce side effects, such as opportunistic infections.

As an alternative approach, it has been proposed to use immunosuppressive monoclonal antibodies (mAbs) against cell-surface molecules, in order to remove specific lymphocyte subsets (depleting antibodies) or to inhibit the function of a target surface molecule without killing the cell bearing it (nondepleting-antibodies).

It is generally agreed that CD4+ T cells play a major part in initiating and maintaining autoimmunity. Accordingly, it has been proposed to use mAbs against CD4+ T cells surface molecules, and in particular anti-CD4 mAbs, as immunosuppressive agents. Although numerous clinical studies confirmed the potential interest of this approach, they also raised several issues to be addressed in order to make anti-CD4 mAbs more suitable for use in routine clinical practice.

By way of example, B-F5 antibody (murine IgG1 anti-human CD4) was tested in different autoimmune diseases:

in rheumatoid arthritis patients, several open studies suggested a positive clinical effect of B-F5 at a daily dose of at least 20 mg (Racadot et al. Clin. Exp. Rheumatol. 10 (4): 365-74; 1992; Wendling et al., Clin. Rheumatol., 11 (4): 542-7, 1992). However, the results observed in a placebo controlled trial with a daily dose of 20 mg for 10 days did not show a significant improvement (Wendling et al. J. Rheumatol.; 25 (8): 1457-61, 1998).

in psoriasis, an improvement in psoriatic lesions was observed following a treatment at a dose of 0.2 mg/kg/day to 0.8 mg/kg/day for 7 or 8 days (Morel et al. J. Autoimmun., 5 (4): 465-77, 1992);

in multiple sclerosis (MS) patients, some positive effects were observed after a 10 days treatment in patients with relapsing-remitting forms, some of who were relapse-free at the 6th month post-therapy (Racadot et al., J. Autoimmun., 6 (6):771-86, 1993); similar effects were observed by Rumbach et al. (MultScler; 1 (4): 207-12, 1996);

in severe Crohn's disease, no significant improvement was observed in patients receiving B-F5 at a dose of 0.5 mg/day/kg for 7 consecutive days or of 0.5 mg/day/kg on the first day (day 0) and of 1 mg/day/kg on days 1-6 (Canva-Delcambre et al., Aliment Pharmacol. Ther. (5):721-7, 1996);

in prevention of allograft rejection, a modification of the biological parameters, indicating an action of B-F5 in vivo at a 30 mg/daily dose was reported. However, it was reported thatB-F5 bioavailability was not sufficient to allow its use for prophylaxis of allograft rejection (Dantal et al. Transplantation, 27; 62(10):1502-6, 1996).

It appears from the above that a first issue to be solved is the need of using high doses of mAb to obtain a clinical improvement. This may result inter alia from the poor accessibility to the mAb of the lymphocytes in the target tissues. The use of higher doses may result in an excessive action on blood lymphocytes, inducing unwanted side effects.

Another drawback of therapy with monoclonal antibodies in humans is that these antibodies are generally obtained from mouse cells, and provoke antimouse responses in the human recipients. This not only results in a lesser efficiency of the treatment and even more of any future treatment with mouse monoclonal antibodies, but also in an increased risk of anaphylaxis.

This drawback can, in principle, be avoided by the use of humanized antibodies, obtained by grafting the complementarity-determining regions (CDRs) of a mouse monoclonal antibody, which determine the antigen-binding specificity, onto the framework regions (FRs) of a human immunoglobulin molecule. The aim of humanization is to obtain a recombinant antibody having the same antigen-binding properties as the mouse monoclonal antibody from which the CDR sequences were derived, and far less immunogenic in humans.

In some cases, substituting CDRs from the mouse antibody for the human CDRs in human frameworks is sufficient to transfer the antigen-binding properties (including not only the specificity, but also the affinity for antigen). However, in many antibodies, some FR residues are important for antigen binding, because they directly contact the antigen in the antibody-antigen complex, or because they influence the conformation of CDRs and thus their antigen binding performance.

Thus, in most cases it is also necessary to substitute one or several framework residues from the mouse antibody for the human corresponding FR residues. Since the number of substituted residues must be as small as possible in order to prevent anti-mouse reactions, the issue is to determine which amino acid residue (s) are critical for retaining the antigen-binding properties. Various methods have been proposed for predicting the more appropriate sites for substitution. Although they provide general principles that may be of some help in the first steps of humanization, the final result varies from an antibody to another. Thus, for a given antibody, it is very difficult to foretell which substitutions will provide the desired result.

BRIEF DESCRIPTION OF THE DRAWINGS

FIG. 1 depicts a DNA sequence encoding mouse B-F5 $V_H$ region (SEQ ID No. 5).

FIG. 2 depicts a DNA sequence encoding mouse B-F5 $V_K$ region (SEQ ID No. 6).

FIG. 3 shows an alignment of the polypeptide sequences of B-F5 (SEQ ID No. 10), FK-001 (SEQ ID Nos. 11, 12, 13, and 14, respectively, from left to right), L4L, and L4M (SEQ ID No. 2).

FIG. 4 shows an alignment of the polypeptide sequences of B-F5 (SEQ ID No. 9, M26 (SEQ ID Nos. 15, 16, 17, and 18, respectively, from left to right), H37L, and H37V (SEQ ID No. 19).

FIG. 5 depicts the fragment of the plasmid encoding the VH region of humanized BF-5; the complete nucleic acid sequence is SEQ ID No. 7, the underlined nucleic acid sequence is SEQ ID No. 3, the amino acid sequence is SEQ ID No. 19).

FIG. 6 depicts the fragment of the plasmid encoding the VK region of humanized BF-5; the complete nucleic acid sequence is SEQ ID No. 8, the underlined nucleic acid sequence is SEQ ID No. 4, the amino acid sequence is SEQ ID No. 2).

FIG. 7 shows the results of the ELISA assays, wherein murine and hB-F5s could moderately inhibit ConA-induced proliferation, but the activities varied from antibody to antibody and/or from donor to donor.

FIG. 8 shows the results of the ELISA assays, wherein murine and hB-F5s were able to inhibit Ag-specific PBMC proliferation induced by PPD.

FIG. 9 shows a test of suppressive activity, wherein the negative control (no activation) is preCD25; 0.5 μg/ml OKT-3 (positive control, full activation) is preCD25-CD3; 5 μg/ml hB-F5 (Test 1) is preCD25-CD4; 30 μg/ml hB-F5 (Test 2) is preCD25-CD4.

DETAILED DESCRIPTION OF THE INVENTION

The inventors have however attempted the humanization of mouse B-F5, and have succeeded in producing humanized B-F5 (hereinafter referred to as hB-F5) having the same CD4 binding properties than parent mouse B-F5.

Furthermore, they have found that, surprisingly, hB-F5 has an in vivo optimal immunosuppressive effect at far lower doses than those previously used with parent B-F5, and than those currently used with other anti-CD4 monoclonal antibodies.

Actually, the inventors have observed that hB-F5 provided an effective immunosuppression, reflected by a positive clinical effect in rheumatoid arthritis patients, when used in a 10 days treatment at a dose as low as 1 mg/day, and preferably at a dose of 5 mg every second day.

The present invention provides a humanized antibody (hB-F5) derived from mouseB-F5 MAb, wherein said hB-F5 antibody has V domains defined by the following polypeptide sequences:

```
- H chain V domain:
                                                 (SEQ ID NO: 1)
EEQLVESGGGLVKPGGSLRLSCAASGFSFSDCRMYWLRQA

PGKGLEWIGVISVKSENYGANYAESVRGRFTISRDDSKNTVYLQMNSLKTEDTAVYYCS

ASYYRYDVGAWFAYWGQGTLVTVSS

- L chain V domain:
                                                 (SEQ ID NO: 2)
DIVMTQSPDSLAVSLGERATINCRASKSVSTSGYSYIYWYQQ

KPGQPPKLLIYLASILESGVPDRFSGSGSGTDFTLTISSLQAEDVAVYYCQHSRELPWTFG

QGTKVEIK.
```

Generally, ahB-F5 antibody of the invention further comprises a human constant region (Fc). This constant region can be selected among constant domains from any class of immunoglobulins, including IgM, IgG, IgD, IgA and IgE, and any isotype, including IgG1, IgG2, IgG3 and IgG4. Preferred constant regions are selected among constant domains of IgG, in particular IgG1.

The present invention also includes any fragment of an hB-F5 antibody comprising the V regions thereof. This comprises in particular Fab, Fab', F (ab)'2, Fv andscFv fragments.

The invention also encompasses a polynucleotide selected among:

a polynucleotide encoding a polypeptide of SEQ ID NO: 1 a polynucleotide encoding a polypeptide of SEQ ID NO: 2.

Preferably, said polynucleotide is selected among:

a polynucleotide of SEQ ID NO: 3;

a polynucleotide of SEQ ID NO: 4.

Polynucleotides of the invention can easily be obtained by the well-known methods of recombinant DNA technology and/or of chemical DNA synthesis.

A polynucleotide encoding the V domain of the H chain or of the L chain of a hB-F5 antibody may be fused with a polynucleotide coding for the constant region of a human H or L chain, for the purpose of expressing the complete H and L chains obtained in this way; a sequence coding a signal peptide allowing the secretion of the protein can also be added. These recombinant polynucleotides are also part of the invention.

The invention also provides expression cassettes wherein a polynucleotide of the invention is linked to appropriate control sequences allowing the regulation of its transcription and translation in a chosen host cell, and recombinant vectors comprising a polynucleotide or an expression cassette of the invention.

These recombinant DNA constructs can be obtained and introduced in host cells by the well-known techniques of recombinant DNA and genetic engineering.

The invention also comprises a host cell, transformed by a polynucleotide of the invention.

Useful host-cells within the framework of the present invention can be prokaryotic or eukaryotic cells. Among suitable eukaryotic cells, one will mention, by way of example, plant cells, cells of yeasts such as Saccharomyces, cells of insects such as Drosophila, or Spodoptera, and mammal cells such as HeLa, CHO, 3T3, C127, BHK, COS, etc. . . .

The construction of expression vectors of the invention, and the transformation of host-cells can be made by the standard techniques of molecular biology.

An hB-F5 antibody of the invention can be obtained by culturing a host cell containing an expression vector comprising a nucleic acid sequence encoding said antibody, under conditions suitable for the expression thereof, and recovering said antibody from the host cell culture.

The present invention also comprises a therapeutic composition comprising a hB-F5 antibody of the invention or a fragment thereof, as defined above.

Preferably, said composition is a composition for parenteral administration, formulated to allow the administration of a dose of from 0.1 to 10 mg, advantageously of from 1 to 5 mg of hB-F5.

More specifically, the invention encompasses the use of an hB-F5 antibody of the invention or a fragment thereof, for preparing an immunosuppressive composition. Said immunosuppressive composition is useful in particular for the treatment or prevention of diseases such as graft rejection, graft-versus-host reaction or host-versus-graft reaction, or autoimmune diseases including for instance myocarditis, diabetes mellitus, psoriasis, lupus erythematosus, Crohn's disease, multiple sclerosis, rheumatoid arthritis, etc.

Moreover, the inventors have found out that hB-F5 was able to activate a particular subset of T CD4+ cells, namely CD4+CD25+ cells.

CD25+CD4+ regulatory T cells (Treg cells) constitute 5-10% of peripheral CD4+ T cells. They were first described in 1995 by Sakaguchi et al. (J. Immunol., 155: 1151-1164) as regulatory cells in mice. When activated, these cells are able to suppress both CD4+ and CD8+ T cell activation and proliferation. Later, CD25+CD4+ suppressor T cells have also been found in humans (Jonuleit et al., J. Exp. Med. 193, 1285-1294, 2001; Levings et al., J. Exp. Med. 193, 1295-1302, 2001; Dieckmann et al., J. Exp. Med. 193, 1303-1310 2001). Numerous articles have been published describing the immunosuppressive role of these cells in different autoimmune disease models and in vitro systems (for review, see for instance Shevach, J. Exp. Med., 193, 11, 41-46, 2001). Ex vivo activated CD4+CD25+ Treg cells have also been shown to be effective at preventing graft-versus-host disease (Taylor et al., Blood, 99, 3493-3499, 2002; Cohen et al., J. Exp. Med. 196, 401-406, 2002; Hoffmann et al., J. Exp. Med. 196, 389-399, 2002). Thus, providing means for activating CD4+CD25+ Treg cells is of great interest.

The invention also relates to the use of the hB-F5 antibody of the invention, or of the parent antibody B-F5, to activate in vitro CD25+CD4+ regulatory T cells.

Preferably, the hB-F5 antibody of the invention is added to the CD25+CD4+ regulatory T cells at a concentration 1 µg/ml from 10 µg/ml.

EXAMPLES

The present invention will be further illustrated by the following additional description, which refers to examples illustrating the properties of hB-F5 antibodies of the invention. It should be understood however that these examples are given only by way of illustration of the invention and do not constitute in any way a limitation thereof.

Example 1: Construction of Humanized B-F5

Design of Humanized B-F5 VH and VK Regions

DNA sequences encoding mouse B-F5 $V_H$ and $V_K$ regions are respectively shown in FIG. 1 and FIG. 2 and under sequence identifiers SEQ ID NO: 5 and SEQ IN ISO: 6. The human $V_H$ and $V_K$ on which the mouse CDRs are grafted were selected by searching databases for human VH most like the original mouse B-F5 $V_H$ and $V_K$. $V_H$ region of a human antibody (M26; Accession Number A36006) had the highest homology with B-F5 $V_H$. $V_K$ region of another human antibody (FK-001; NAKATANI et al., Biotechnology, 7 (1989), 805-810)) had the highest homology with B-F5 $V_K$.

Two types of $V_K$ differing between them in that the 4th residue was Leucine or Methionine were constructed and designated as L4L and L4M. Two types of VH differing between them in that the 37th amino acid residue was Leucine or Valine, were constructed and designated as H37L and H37V. The alignment of the polypeptide sequences of B-F5, FK-001, L4L, and L4M is shown in FIG. 3. The alignment of the polypeptide sequences of B-F5, M26, H37L, and H37V is shown in FIG. 4. The FR residues previously reported to be important for the packing of CDRs (Chothia et al., Nature, 342 (1989), 877; Foote et al., J. Mol. Biol., 224 (1992), 487) are boxed.

By combining these VH and VK, 4 versions of V regions were designed.

Expression of Humanized B-F5

The subsequent steps for production of humanized B-F5 were the same as those disclosed in U.S. Pat. No. 5,886,152 for humanizedB-B10.

Briefly, expression plasmids for the H chain (VH humanized region fused to the constant region of a humany-1 chain (TAKAHASHI et al., Cell, 29 (1982), 671-679)) and the L chain (VK humanized region fused to the constant region of FK-001K chain) of humanized B-F5 were constructed separately. In these plasmids, the expression of humanized B-F5 is driven by the promoter/enhancer of the gene of human monoclonal IgM, FK-001. FIGS. 5 and 6 respectively show the fragments of the plasmids encoding the VH and VK regions of humanized BF-5. The sequences encoding the V region are underlined and the corresponding polypeptide sequences are indicated above the nucleotide sequence. Both plasmids and pSV2neo were simultaneously introduced into mouse myeloma Sp2/0 (ATCC CRL-1581) using Lipofectin. Transfectomas producing human IgG were selected by ELISA, using an anti-human IgG (y chain) antibody and an anti-human Ig K chain antibody.

Example 2: Characterisation of the Different Versions of Humanized

B-F5 Estimation of CD4 Binding Activity

Culture supernatants of transfectomas producing the four versions of hB-F5 were collected, and concentrated. The different antibodies were purified from culture supernatants by affinity chromatography using protein A Sepharose and assessed for their CD4 binding activity by measuring, by means of competitive ELISA, their inhibitory activities against the binding of biotinylated mB-F5 to soluble CD4 coated on microtiter plates. Incubation time is 2 hours for 37 C and overnight for 4 C.

The relative binding activities of hB-F5s (binding activity of mB-F5 was taken as 100%) are shown in Table I below

TABLE I

| Antibody | Temp (° C.) | Relative binding activity (% of mB-F5) |
|---|---|---|
| H37L/L4L | 4 | 80 |
|  | 37 | 30 |
| H37L/L4M | 4 | 80 |
|  | 37 | 30 |
| H37V/L4L | 4 | 10-20 |
|  | 37 | 10 |
| H37V/L4M | 4 | 10-20 |
|  | 37 | 10 |

From the results shown in Table I, it appears that the 37th residue of $V_H$, Leucine, is critical to maintain CD4 binding activity of hB-F5 because the CD4 binding activity is several-fold reduced by conversion of $^{37}$Leu to $^{37}$Val. On the contrary, the $4^{th}$ residue of V is found to be not so important for the CD4 binding activity. As the structural difference between $^{37}$Leu and $^{37}$Val of $V_H$ is not clearly demonstrated by molecular modeling, the superiority of H37L to H37V in CD4 binding activity was unexpected.

H37L/L4L and H37L/L4M were chosen for evaluating the in vitro biological activities.

Investigation of the In Vitro Biological Activities of Humanized B-F5

The in vitro biological activities of mouse B-F5 and humanized B-F5s (H37L/L4M IgG1 and H37L/L4L IgG 1) were evaluated. Humanized B-F5s of IgG2 type (H37L/L4M IgG2 and H37L/L4L IgG2) were also tested.

The in vitro biological activities of mB-F5 and the four types of hB-F5s were evaluated using peripheral blood mononuclear cells (PBMCs) from healthy donors. PBMCs were activated by ConA (2.5 μg/ml, 3 days) of PPD (10 μg/ml, 4 days) in the presence of murine or hB-F5s, and were monitored for their proliferative responses by $^3$H-thymidine incorporation.

The results are shown in FIGS. 7 and 8. Murine and hB-F5s could moderately inhibit ConA-induced proliferation, but the activities varied from antibody to antibody and/or from donor to donor (FIG. 7). Also, murine and hB-F5s were able to inhibit Ag-specific PBMC proliferation induced by PPD (FIG. 8).

IgG1 type of hB-F5 inhibited PPD-induced proliferation more effectively (as high as 70% inhibition, FIGS. 7 and 8) than Mb-F5. IgG1 type seemed to be more effective than IgG2 type of which inhibitory activity was almost the same as mB-F5. For IgG2 type of H37L/L4M and H37L/L4L inhibitory activities of B-F5s against PPD-induced PMBC proliferation were as follows: H37L/L4M IgG1>H37L/L4L IgG1>H37L/L4M IgG2=H37L/L4L IgG2=mB-F5.

Considering the efficacy of the in vitro biological activity and the smaller number of mouse amino acids, H37L/L4M IgG1 was chosen for further evaluation.

Example 3: Preliminary Evaluation of the Effect of Hb-F50N Patients with Reheumatoid Arthritis (RA)

The Effect of hB-F5 (H37L/L4M IgG1) was Tested on RA Patients.

The conditions of the assay are as follows:

Each patient received a 10 days treatment consisting of 5 injections of 5 mg of hB-F5 (an injection every 2nd day).

The results for 3 different patients are shown in Tables II-IV below:

Patient 1 (Table II):

Diagnosis: Rheumatoid Arthritis, Activity 2

Rheumatoid factor: 2; Stage: 2

Sex: F; Age: 65; Onset of the disease: 1965

Additional therapy: Diclophenac 150 mg/day

TABLE II

| | | Before | During treatment (days) | | | | | After treatment (weeks) |
|---|---|---|---|---|---|---|---|---|
| Clinical Investigations | | Treatment | 2 | 4 | 6 | 8 | 10 | 4 |
| Estimation of pain in joints (0-10) | | 4.5 | 2 | 2 | 1.5 | 3 | 2.2 | 3.5 |
| Morning stiffness in minutes | | 360 | 0 | 0 | 90 | 90 | 120 | 20 |
| Severity of condition (1-5) | Physician | 3 | 3 | 3 | 2.5 | 3 | 3 | 3 |
| | Patient | 3 | 3 | 3 | 3 | 3 | 3 | 3 |
| Number of swollen joints | | 6 | 6 | 4 | 3 | 2 | 2 | 7 |
| Number of painful joints | | 25 | 12 | 6 | 7 | 13 | 13 | 23 |
| Swelling index (0-30) | | 8 | 6 | 4 | | 2 | 3 | 9 |
| Power in hand | Right | 17 | 15 | 20 | 22 | 12 | 20 | 15 |
| | Left | 10 | 10 | 10 | 15 | 12 | 19 | 12 |
| Estimation of tiredness (0-10) | | 7.7 | 4 | 2.3 | 2 | 2.3 | 3.1 | 3 |
| Estimation of treatment effects | Patent | | 3 | 3 | 4 | 3 | 5 | 2 |
| | Physician | | 3 | 3 | 4 | 3 | 5 | 2 |
| Erythrocyte sedimentation rate | | 35 | | | | | 34 | 25 |
| C-Reactive Protein | | 4.0 | | | | | 2 | 2.5 |

Patient 2 (Table III):

Diagnosis: Rheumatoid Arthritis, Activity 3

Rheumatoid factor: 2; Stage: 2

Sex: F; age: 48 Onset of the disease: 2000

Additional therapy. Diclophenac 150 mg/day

TABLE III

| Clinical Investigations | Before Treatment | During treatment (days) | | | | | After treatment (weeks) |
|---|---|---|---|---|---|---|---|
| | | 2 | 4 | 6 | 8 | 10 | 4 |
| Estimation of pain in joints (0-10) | 8.2 | | 8.2 | 5 | 2.9 | 2.2 | 0.6 |
| Morning stiffness in minutes | 240 | | 120 | 120 | 60 | 20 | 10 |
| Severity of condition (1-5)  Physician | 4 | | 3 | 3 | 3 | 3 | 2 |
| Severity of condition (1-5)  Patient | 4 | | 4 | 3 | 3 | 3 | 2 |
| Number of swollen joints | 13 | | 12 | 11 | 11 | 5 | 5 |
| Number of painful joints | 22 | | 22 | 16 | 15 | 13 | 7 |
| Swelling index (0-30) | 15 | | 14 | 12 | 11 | 5 | 5 |
| Power in hand   Right | 30 | | 30 | 28 | 34 | 36 | 40 |
| Power in hand   Left | 22 | | 20 | 18 | 18 | 22 | 28 |
| Estimation of tiredness (0-10) | 8.7 | | 5.1 | 2.2 | 2.2 | 1.1 | 0.7 |
| Estimation of treatment effects  Patent | | | 3 | 4 | 4 | 4/5 | 5 |
| Estimation of treatment effects  Physician | | | 3 | 2 | 3 | 4/5 | 5 |
| Erythrocyte sedimentation rate | 35 | | | | | 38 | 35 |
| C-Reactive Protein | 1.2 | | | | | 0.2 | 0.8 |

Patient 3 (Table IV):
Diagnosis: Rheumatoid Arthritis, Activity 3
Rheumatoid factor: 3; Stage: 2
Sex: F; Age: 49; Onset of the disease: 1989
Additional therapy. Diclophenac 150 mg/day

TABLE IV

| Clinical Investigations | Before Treatment | During treatment (days) | | | | | | After treatment (weeks) |
|---|---|---|---|---|---|---|---|---|
| | | 2 | 4 | 6 | 8 | 10 | 1 | 2 |
| Estimation of pain in joints (0-10) | 7.9 | 7.6 | 7.6 | 7.2 | 5.0 | 3.0 | 1.5 | 1.3 |
| Morning stiffness in minutes | 360 | 0 | 0 | 0 | 0 | 0 | 0 | |
| Severity of condition (1-5)  Physician | 4 | 3 | 3 | 3 | 3 | 3 | 2 | 2 |
| Severity of condition (1-5)  Patient | 5 | 4 | 4 | 3 | | 3 | 2 | 2 |
| Number of swollen joints | 10 | 7 | 7 | 6 | 5 | 5 | 5 | 5 |
| Number of painful joints | 30 | 24 | 24 | 15 | 11 | 11 | 10 | 9 |
| Swelling index (0-30) | 15 | 12 | 12 | 9 | 7 | 7 | 6 | |
| Power in hand   Right | 24 | 30 | 30 | 36 | 48 | 48 | 50 | 50 |
| Power in hand   Left | 24 | 30 | 30 | 38 | 40 | 34 | 40 | 42 |
| Estimation of tiredness (0-10) | 8.5 | 7.2 | 5.2 | 0 | 0 | 0 | 0 | 0 |
| Estimation of treatment effects  Patent | | 3 | 3 | 3 | | 5 | 5 | 5 |
| Estimation of treatment effects  Physician | | 3 | 4/3 | 4 | 4 | 5 | 5 | 5 |
| Erythrocyte sedimentation rate | 61 | | 53 | 42 | 45 | | | 41 |
| C-Reactive Protein | 8 | | | | 3.7 | | | 3.3 |

Example 4: Activation of CD4+CD25+ Treg Cells by hB-F5

Figure 9:
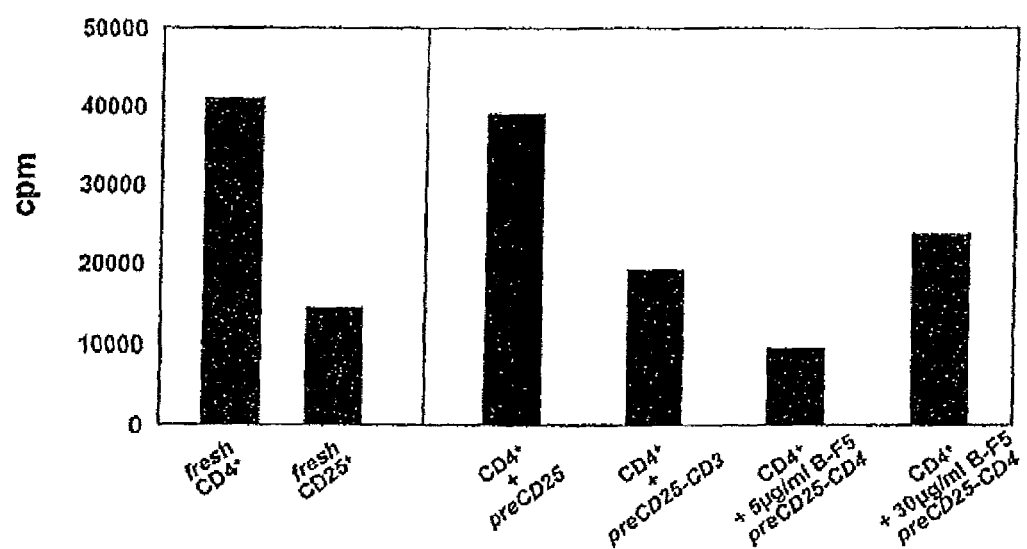

Isolation of T cells:
1) T regulatory Cells (Tregs):
   CD25+ cells are isolated using CD25 microbeads;
   Depletion of contaminations: CD14−, CD8−, CD19− positive cells is made with CD14/CD8/CD19 DYNALbeads;
   Depletion of CD45RA+ cells is made with CD45RA mAb+anti-mouse DYNALbeads: purity: >95% CD4+CD25+ Tregs
2) Effector Cells
   CD4+ T cells are isolated using CD4 microbeads
   Depletion of CD45RO+ cells is made with CD45RO+ mAb+anti-mouse DYNALbeads; purity: >98% CD4/CD45RA+, CD25− effector T cells 3) Test System:
   CD25+ Tregs from donor A are cocultured for 2 days with syngenic CD2-depleted PBMC, without additions (negative control=no activation=no suppressive activity), or in the presence of 0.5 µg/ml anti-CD3 (OKT-3=positive control=full activation of Tregs), or in the presence of 5 µg/ml or 30 µg/ml hB-F5.
   After extensive washing of pre-cultured cells, CD25+ Tregs cells are isolated and treated by y-radiation (3000 rad).
4) Test of Suppressive Activity:
   Pre-cultured CD25+ Tregs cells are cocultured for 4 days with freshly isolated CD4+ effector T cells (1:1) from donor B in the presence of APC's (CD2-depleted PBMC) from donor A (syngenic for pre-cultured T cells (no additional activation), allogeneic for effector T cells (=allogeneic mixed lymphocyte reaction). Then, cells are incubated for 16 h with 3H Thymidine, and proliferation of effector T cells is detected.
   The results are shown in FIG. 9.
   Legend of FIG. 9:
   negative control (no activation)=preCD25;

0.5 μg/ml OKT-3 (positive control, full activation)=preCD25-CD3;

5 μg/ml hB-F5(Test-1)=preCD25-CD4;
30 μg/ml hB-F5 (Test-2)=preCD25-CD4.

What is claimed is:

1. A humanized anti-CD4 antibody which is a humanized version of a mouse monoclonal anti-CD4 antibody, wherein the mouse monoclonal anti-CD4 antibody comprises a Vh region having SEQ ID NO: 9 and a Vk region having SEQ ID NO: 10, and wherein the humanized anti-CD4 antibody further comprises an IgG1 constant domain.

2. A humanized anti-CD4 antibody which comprises an L chain V domain having the complementarity-determining regions of SEQ ID NO: 2 shown in FIG. 3 and an H chain V domain having the complementarity-determining regions of SEQ ID NO: 1 shown in FIG. 4, wherein the H chain V domain further comprises a Leucine residue at the position 37, and wherein the humanized anti-CD4 antibody further comprises an IgG1 constant domain.

3. A humanized anti-CD4 antibody according to claim 2 which comprises an H chain V domain having SEQ ID NO: 1 and an L chain V domain having SEQ ID NO: 2, and wherein the humanized anti-CD4 antibody further comprises an IgG1 constant domain.

4. A therapeutic composition comprising the humanized anti-CD4 antibody of claim 1.

5. A method of making a humanized anti-CD4 antibody according to claim 3 comprising the steps of:
- culturing a host cell comprising a polynucleotide encoding SEQ ID NO: 1 and a polynucleotide encoding SEQ ID NO: 2, under conditions suitable for expression thereof, and
- recovering the expressed humanized anti-CD4 antibody.

6. A method according to claim 5 wherein the host cell is a mammalian cell.

7. A method according to claim 6 wherein the mammalian cell is a CHO cell.

8. A method according to claim 6 wherein the mammalian cell is a Sp2/0 cell.

9. A method according to claim 5 further comprising a step of purifying the expressed humanized anti-CD4 antibody by affinity chromatography using protein A Sepharose.

10. A method according to claim 7 further comprising a step of purifying the expressed humanized anti-CD4 antibody by affinity chromatography using protein A Sepharose.

11. A method according to claim 8 further comprising a step of purifying the expressed humanized anti-CD4 antibody by affinity chromatography using protein A Sepharose.

12. A method of treating a subject suffering from an autoimmune disease comprising administering to said subject an antibody according to claim 1.

13. A polynucleotide comprising a DNA molecule encoding the antibody of claim 1.

14. A method of using the humanized antibody of claim 1 to activate CD25+CD4+ regulatory T cells comprising contacting the humanized antibody with $CD25^+CD4^+$ regulatory T cells in vitro.

15. A method of preventing graft rejection in a subject comprising administering to said subject the therapeutic composition of claim 4.

* * * * *

SEQUENCE LISTING

```
<160> NUMBER OF SEQ ID NOS: 18

<210> SEQ ID NO 1
<211> LENGTH: 124
<212> TYPE: PRT
<213> ORGANISM: Artificial sequence
<220> FEATURE:
<223> OTHER INFORMATION: V domain of H chain of humanized antibody hBF-5

<400> SEQUENCE: 1

Glu Glu Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asp Cys
            20                  25                  30

Arg Met Tyr Trp Val Arg Gln Ala Pro Gly Lys Gly Leu Glu Trp Ile
        35                  40                  45

Gly Val Ile Ser Val Lys Ser Glu Asn Tyr Gly Ala Asn Tyr Ala Glu
    50                  55                  60

Ser Val Arg Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Ala Ser Tyr Tyr Arg Tyr Asp Val Gly Ala Trp Phe Ala
            100                 105                 110

Tyr Trp Gly Gln Gly Thr Leu Val Thr Val Ser Ser
        115                 120

<210> SEQ ID NO 2
<211> LENGTH: 111
<212> TYPE: PRT
<213> ORGANISM: Artificial sequence
<220> FEATURE:
<223> OTHER INFORMATION: V domain of K chain of humanized antibody hBF-5

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile Tyr Trp Tyr Gln Gln Lys Pro Gly Gln Pro Pro
        35                  40                  45

Lys Leu Leu Ile Tyr Leu Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Trp Thr Phe Gly Gln Gly Thr Lys Val Glu Ile Lys
            100                 105                 110

<210> SEQ ID NO 3
<211> LENGTH: 372
<212> TYPE: DNA
<213> ORGANISM: Artificial sequence
<220> FEATURE:
<223> OTHER INFORMATION: V domain of H cahin of humanized antibody hBF-5

<400> SEQUENCE: 3
```

```
gaggaacagc ttgtggagtc tgggggaggc ttggtgaaac ccggaggttc tctgaggctc      60
tcctgtgcag cctcgggttt cagtttcagt gactgccgga tgtactgggt tcgccaggct     120
ccagggaagg ggctggagtg gattggtgtg atttcagtca atctgagaa ttatggagca     180 aattatgcag agtctgtgag gggcagattc actatttcaa gagatgattc aaaaaacacg     240
gtctatctgc agatgaacag cttgaagacc gaagacactg ccgtttatta ttgtagtgcc     300
tcctattata ggtacgacgt gggggcctgg tttgcttact ggggccaagg gactctggtc     360
actgtctctt ca                                                        372

<210> SEQ ID NO 4
<211> LENGTH: 333
<212> TYPE: DNA
<213> ORGANISM: Artificial sequence
<220> FEATURE:
<223> OTHER INFORMATION: V domain of K chain of humanized antibody hBF-5

<400> SEQUENCE: 4
gacatcgtga tgacccagtc tccagactcc ctggctgtgt ctctgggcga gagggccacc      60
atcaactgca gggccagcaa aagtgtcagt acatctggct acagttatat atattggtac     120
cagcagaaac caggacagcc tcctaagctg ctcatttacc ttgcatccat cctagaatct     180
ggggtccctg accgattcag tggcagcggg tctgggacag atttcactct caccatcagc     240
agcctgcagg ctgaagatgt ggcagtttat tactgtcagc acagtaggga acttccgtgg     300
acgttcggcc aagggaccaa ggtggaaatc aaa                                  333

<210> SEQ ID NO 5
<211> LENGTH: 372
<212> TYPE: DNA
<213> ORGANISM: Mus musculus

<400> SEQUENCE: 5
caggaatacc ttgtggagac cggggaggc ttggtgaggc ctggaaattc tctgaaactc      60
tcctgtgtca cctcgggttt cagtttcagt gactgccgga tgtactggct tcgccagcct     120
ccagggaagg ggctggagtg gattggtgtg atttcagtca atctgagaa ttatggagca     180 aattatgcag agtctgtgag gggcagattc actatttcaa gagatgattc aaaaagcagt     240
gtctatctgc agatgagcag attgagagag gaagacactg ccacttatta ttgtagtgcc     300
tcctattata ggtacgacgt gggggcctgg tttgcttact ggggccaagg gactctggtc     360
actgtctctg ca                                                        372

<210> SEQ ID NO 6
<211> LENGTH: 383
<212> TYPE: DNA
<213> ORGANISM: Mus musculus

<400> SEQUENCE: 6
gacattgtgc tgacacagtc tccttcttcc ttagttgtat ctctggggca gagggccacc      60
atctcatgca gggccagcaa aagtgtcagt acatctggct acagttatat atattggtac     120
caacagatcc caggacagcc acccaaactc ctcatctatc ttgcatccat cctagaatct     180
ggggtccctg gcaggttcag tggcagtggg tctgggacag acttcaccct caacatccat     240
cctgtggagg aggaggatgc tgcaacctat tactgtcagc acagtaggga acttccgtgg     300
acgttcggtg gaggcaccaa gctggagatc aaacgggctg atgctgcacc aactgtatcc     360
```

```
atcttcccac catccagtga gca                                            383
```

<210> SEQ ID NO 7
<211> LENGTH: 550
<212> TYPE: DNA
<213> ORGANISM: Artificial Sequence
<220> FEATURE:
<223> OTHER INFORMATION: Part of plasmid encoding V domain of H chain of
      humanized antibody hB-F5

<400> SEQUENCE: 7

```
gaggagctcc agacaatgtc tgtctccttc ctcatcttcc tgcccgtgct gggcctccca     60
tggggtcagt gtcagggaga tgccgtattc acagcagcat tcacagactg aggggtgttt    120
cactttgctg tttccttttg tctccaggtg tcctgtcaga ggaacagctt gtggagtctg    180
ggggaggctt ggtgaaaccc ggaggttctc tgaggctctc ctgtgcagcc tcggtttca     240
gtttcagtga ctgccggatg tactgggttc gccaggctcc agggaagggg ctggagtgga    300
ttggtgtgat tcagtcaaa tctgagaatt atggagcaaa ttatgcagag tctgtgaggg    360
gcagattcac tatttcaaga gatgattcaa aaaacacggt ctatctgcag atgaacagct    420
tgaagaccga agacactgcc gtttattatt gtagtgcctc ctattatagg tacgacgtgg    480
gggcctggtt tgcttactgg ggccaaggga ctctggtcac tgtctcttca ggtaagaatg    540
gccaagcttg                                                          550
```

<210> SEQ ID NO 8
<211> LENGTH: 498
<212> TYPE: DNA
<213> ORGANISM: Artificial Sequence
<220> FEATURE:
<223> OTHER INFORMATION: Part of plasmid encoding V domain of K chain of
      humanized antibody hB-F5

<400> SEQUENCE: 8

```
ggaggatcca attatctgct gacttataat actactagaa agcaaattta atgacatat     60
ttcaattata tctgagacag cgtgtataag tttatgtata atcattgtcc attcctgact    120
acaggtgcct acggggacat cgtgatgacc cagtctccag actccctggc tgtgtctctg    180
ggcgagaggg ccaccatcaa ctgcagggcc agcaaaagtg tcagtacatc tggctacagt    240
tatatatatt ggtaccagca gaaaccagga cagcctccta agctgctcat ttaccttgca    300
tccatcctag aatctggggt ccctgaccga ttcagtggca gcgggtctgg gacagatttc    360
actctcacca tcagcagcct gcaggctgaa gatgtggcag tttattactg tcagcacagt    420
agggaacttc cgtggacgtt cggccaaggg accaaggtgg aaatcaaacg tgagtagaat    480
ttaaatttta agcttctt                                                 498
```

<210> SEQ ID NO 9
<211> LENGTH: 124
<212> TYPE: PRT
<213> ORGANISM: Mus musculus

<400> SEQUENCE: 9

```
Gln Glu Tyr Leu Val Glu Thr Gly Gly Gly Leu Val Arg Pro Gly Asn
 1               5                  10                  15

Ser Leu Lys Leu Ser Cys Val Thr Ser Gly Phe Ser Phe Ser Asp Cys
            20                  25                  30

Arg Met Tyr Trp Leu Arg Gln Pro Pro Gly Lys Gly Leu Glu Trp Ile
        35                  40                  45
```

```
Gly Val Ile Ser Val Lys Ser Glu Asn Tyr Gly Ala Asn Tyr Ala Glu
        50                  55                  60

Ser Val Arg Gly Arg Phe Thr Ile Ser Arg Asp Asp Ser Lys Ser Ser
 65                  70                  75                  80

Val Tyr Leu Gln Met Ser Arg Leu Arg Glu Glu Asp Thr Ala Thr Tyr
                 85                  90                  95

Tyr Cys Ser Ala Ser Tyr Tyr Arg Tyr Asp Val Gly Ala Trp Phe Ala
                100                 105                 110

Tyr Trp Gly Gln Gly Thr Leu Val Thr Val Ser Ala
            115                 120
```

<210> SEQ ID NO 10
<211> LENGTH: 111
<212> TYPE: PRT
<213> ORGANISM: Mus musculus

<400> SEQUENCE: 10

```
Asp Ile Val Leu Thr Gln Ser Pro Ser Ser Leu Val Val Ser Leu Gly
  1               5                  10                  15

Gln Arg Ala Thr Ile Ser Cys Arg Ala Ser Lys Ser Val Ser Thr Ser
                 20                  25                  30

Gly Tyr Ser Tyr Ile Tyr Trp Tyr Gln Gln Ile Pro Gly Gln Pro Pro
             35                  40                  45

Lys Leu Leu Ile Tyr Leu Ala Ser Ile Leu Glu Ser Gly Val Pro Gly
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Trp Thr Phe Gly Gly Gly Thr Lys Leu Glu Ile Lys
                100                 105                 110
```

<210> SEQ ID NO 11
<211> LENGTH: 23
<212> TYPE: PRT
<213> ORGANISM: Homo sapiens

<400> SEQUENCE: 11

```
Asp Ile Val Met Thr Gln Ser Pro Asp Ser Leu Ala Val Ser Leu Gly
  1               5                  10                  15

Glu Arg Ala Thr Ile Asn Cys
                 20
```

<210> SEQ ID NO 12
<211> LENGTH: 15
<212> TYPE: PRT
<213> ORGANISM: Homo sapiens

<400> SEQUENCE: 12

```
Trp Tyr Gln Gln Lys Pro Gly Gln Pro Pro Lys Leu Leu Ile Tyr
  1               5                  10                  15
```

<210> SEQ ID NO 13
<211> LENGTH: 32
<212> TYPE: PRT
<213> ORGANISM: Homo sapiens

<400> SEQUENCE: 13

```
Gly Val Pro Asp Arg Phe Ser Gly Ser Gly Ser Gly Thr Asp Phe Thr
  1               5                  10                  15
```

```
Leu Thr Ile Ser Ser Leu Gln Ala Glu Asp Val Ala Val Tyr Tyr Cys
            20                  25                  30

<210> SEQ ID NO 14
<211> LENGTH: 10
<212> TYPE: PRT
<213> ORGANISM: Homo sapiens

<400> SEQUENCE: 14

Phe Gly Gln Gly Thr Lys Val Glu Ile Lys
1               5                   10

<210> SEQ ID NO 15
<211> LENGTH: 30
<212> TYPE: PRT
<213> ORGANISM: Homo sapiens

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 16
<211> LENGTH: 14
<212> TYPE: PRT
<213> ORGANISM: Homo sapiens

<400> SEQUENCE: 16

Trp Val Arg Gln Ala Pro Gly Lys Gly Leu Glu Trp Val Gly
1               5                   10

<210> SEQ ID NO 17
<211> LENGTH: 32
<212> TYPE: PRT
<213> ORGANISM: Homo sapiens

<400> SEQUENCE: 17

Arg Phe Thr Ile Ser Arg Asp Asp Ser Lys Asn Thr Leu Tyr Leu Gln
1               5                   10                  15

Met Asn Ser Leu Lys Thr Glu Asp Thr Ala Val Tyr Tyr Cys Thr Thr
            20                  25                  30

<210> SEQ ID NO 18
<211> LENGTH: 11
<212> TYPE: PRT
<213> ORGANISM: Homo sapiens

<400> SEQUENCE: 18

Trp Gly Gln Gly Thr Leu Val Thr Val Ser Ser
1               5                   10
```